(12) United States Patent
Amaya et al.

(10) Patent No.: US 11,596,337 B2
(45) Date of Patent: Mar. 7, 2023

(54) METHODS AND SYSTEMS FOR OPERATING AN INTRAOPERATIVE NEUROPHYSIOLOGICAL MONITORING SYSTEM IN CONJUNCTION WITH ELECTROCAUTERY PROCEDURES

(71) Applicant: Cadwell Laboratories, Inc, Kennewick, WA (US)

(72) Inventors: Ivan Amaya, Richland, WA (US); Michael Batdorf, Benton City, WA (US); Ross Delvin, Kennewick, WA (US); Jason McCann, Richland, WA (US); John A. Cadwell, Richland, WA (US); Ethan Rhodes, Benton City, WA (US); Richard A. Villarreal, West Richland, WA (US)

( * ) Notice: Subject to any disclaimer, the term of this patent is extended or adjusted under 35 U.S.C. 154(b) by 846 days.

(21) Appl. No.: 16/393,140

(22) Filed: Apr. 24, 2019

(65) Prior Publication Data

US 2020/0337575 A1    Oct. 29, 2020

Related U.S. Application Data

(60) Provisional application No. 62/772,753, filed on Nov. 29, 2018, provisional application No. 62/662,138, filed on Apr. 24, 2018.

(51) Int. Cl.
*A61B 5/24* (2021.01)
*A61B 5/00* (2006.01)
(Continued)

(52) U.S. Cl.
CPC ............... *A61B 5/24* (2021.01); *A61B 5/369* (2021.01); *A61B 5/389* (2021.01); *A61B 5/4041* (2013.01);
(Continued)

(58) Field of Classification Search
CPC ........... A61B 5/24; A61B 5/369; A61B 5/389; A61B 5/4041; A61B 5/4893;
(Continued)

(56) References Cited

U.S. PATENT DOCUMENTS 751,475 A    2/1904   De Vilbiss
2,320,709 A  6/1943   Arnesen
(Continued)

FOREIGN PATENT DOCUMENTS

CN    104766176 A      7/2015
DE    102014008684 A1  1/2016
(Continued)

OTHER PUBLICATIONS

Aage R. Møller, "Intraoperative Neurophysiologic Monitoring", University of Pittsburgh, School of Medicine Pennsylvania, © 1995 by Harwood Academic Publishers GmbH.
(Continued)

*Primary Examiner* — Jung Kim
(74) *Attorney, Agent, or Firm* — Novel IP

(57) ABSTRACT

Methods and systems for conditioning a signal indicative of electrosurgical unit activity are described. A hardware circuit acquires AC current from an electrosurgical unit on patient isolated circuitry and conditions the signal in either of two alternate processing methods. The processed signal is routed as input to an analog to digital converter circuit. A method for determining saturation on referential inputs and recovering inputs to an unsaturated state is also described.

18 Claims, 12 Drawing Sheets

(51) Int. Cl.
 *A61B 18/14* (2006.01)
 *A61B 5/369* (2021.01)
 *A61B 5/389* (2021.01)

(52) U.S. Cl.
 CPC .......... *A61B 5/4893* (2013.01); *A61B 5/7217* (2013.01); *A61B 18/14* (2013.01); *A61B 5/4836* (2013.01); *A61B 5/6843* (2013.01)

(58) Field of Classification Search
 CPC ..... A61B 5/7217; A61B 18/14; A61B 5/4836; A61B 5/6843; A61B 18/1442; A61B 2018/00595; A61B 2018/167
 See application file for complete search history.

(56) References Cited

U.S. PATENT DOCUMENTS

| | | | |
|---|---|---|---|
| 2,807,259 | A | 9/1957 | Guerriero |
| 2,950,437 | A | 8/1960 | Stahl |
| 3,165,340 | A | 1/1965 | Kuehl |
| 3,659,250 | A | 4/1972 | Horton |
| 3,682,162 | A | 8/1972 | Colyer |
| 3,985,125 | A | 10/1976 | Rose |
| 3,993,859 | A | 11/1976 | McNeel |
| 4,155,353 | A | 5/1979 | Rea |
| 4,262,306 | A | 4/1981 | Renner |
| 4,263,899 | A | 4/1981 | Burgin |
| 4,545,374 | A | 10/1985 | Jacobson |
| 4,562,832 | A | 1/1986 | Wilder |
| 4,616,635 | A | 10/1986 | Caspar |
| 4,705,049 | A | 11/1987 | John |
| 4,716,901 | A | 1/1988 | Jackson |
| 4,743,959 | A | 5/1988 | Frederiksen |
| 4,765,311 | A | 8/1988 | Kulik |
| 4,817,587 | A | 4/1989 | Janese |
| 4,862,891 | A | 9/1989 | Smith |
| 4,889,502 | A | 12/1989 | Althouse |
| 4,914,508 | A | 4/1990 | Music |
| 5,107,845 | A | 4/1992 | Guern |
| 5,171,279 | A | 12/1992 | Mathews |
| 5,196,015 | A | 3/1993 | Neubardt |
| 5,284,153 | A | 2/1994 | Raymond |
| 5,284,154 | A | 2/1994 | Raymond |
| 5,299,563 | A | 4/1994 | Seton |
| 5,377,667 | A | 1/1995 | Patton |
| 5,438,989 | A | 8/1995 | Hochman |
| 5,462,448 | A | 10/1995 | Kida |
| 5,472,426 | A | 12/1995 | Bonati |
| 5,474,558 | A | 12/1995 | Neubardt |
| 5,540,235 | A | 7/1996 | Wilson |
| 5,544,286 | A | 8/1996 | Laney |
| 5,560,372 | A | 10/1996 | Cory |
| 5,565,779 | A | 10/1996 | Arakawa |
| 5,578,060 | A | 11/1996 | Pohl |
| 5,601,608 | A | 2/1997 | Mouchawar |
| 5,602,585 | A | 2/1997 | Dickinson |
| 5,625,759 | A | 4/1997 | Freeman |
| 5,648,815 | A | 7/1997 | Toba |
| 5,664,029 | A | 9/1997 | Callahan |
| 5,681,265 | A | 10/1997 | Maeda |
| 5,684,887 | A | 11/1997 | Lee |
| 5,728,046 | A | 3/1998 | Mayer |
| 5,741,261 | A | 4/1998 | Moskovitz |
| 5,766,133 | A | 6/1998 | Faisandier |
| 5,772,661 | A | 6/1998 | Michelson |
| 5,775,331 | A | 7/1998 | Raymond |
| 5,775,931 | A | 7/1998 | Jones |
| 5,785,648 | A | 7/1998 | Min |
| 5,792,044 | A | 8/1998 | Foley |
| 5,795,291 | A | 8/1998 | Koros |
| 5,830,150 | A | 11/1998 | Palmer |
| 5,847,755 | A | 12/1998 | Wixson |
| 5,860,973 | A | 1/1999 | Michelson |
| 5,868,668 | A | 2/1999 | Weiss |
| 5,885,210 | A | 3/1999 | Cox |
| 5,891,147 | A | 4/1999 | Moskovitz |
| 5,928,139 | A | 7/1999 | Koros |
| 5,928,158 | A | 7/1999 | Aristides |
| 5,930,379 | A | 7/1999 | Rehg |
| 5,931,777 | A | 8/1999 | Sava |
| 5,933,929 | A | 8/1999 | Kawakami |
| 5,944,658 | A | 8/1999 | Koros |
| 5,954,635 | A | 9/1999 | Foley |
| 5,993,385 | A | 11/1999 | Johnston |
| 6,004,312 | A | 12/1999 | Finneran |
| 6,004,341 | A | 12/1999 | Zhu |
| 6,026,180 | A | 2/2000 | Wittenstein |
| 6,042,540 | A | 3/2000 | Johnston |
| 6,062,216 | A | 5/2000 | Corn |
| 6,074,343 | A | 6/2000 | Nathanson |
| 6,088,878 | A | 7/2000 | Antonucci |
| 6,095,987 | A | 8/2000 | Shmulewitz |
| 6,109,948 | A | 8/2000 | Kuo |
| 6,116,941 | A | 9/2000 | Kuo |
| 6,119,306 | A | 9/2000 | Antonucci |
| 6,139,493 | A | 10/2000 | Koros |
| 6,152,871 | A | 11/2000 | Foley |
| 6,181,961 | B1 | 1/2001 | Prass |
| 6,196,969 | B1 | 3/2001 | Bester |
| 6,200,331 | B1 | 3/2001 | Swartz |
| 6,206,826 | B1 | 3/2001 | Mathews |
| 6,210,202 | B1 | 4/2001 | Kuo |
| 6,224,545 | B1 | 5/2001 | Cocchia |
| 6,236,874 | B1 | 5/2001 | Devlin |
| 6,241,548 | B1 | 6/2001 | Kuo |
| 6,259,945 | B1 | 7/2001 | Epstein |
| 6,264,491 | B1 | 7/2001 | Lord |
| 6,266,558 | B1 | 7/2001 | Gozani |
| 6,273,740 | B1 | 8/2001 | Lord |
| 6,287,322 | B1 | 9/2001 | Zhu |
| 6,302,842 | B1 | 10/2001 | Auerbach |
| 6,306,100 | B1 | 10/2001 | Prass |
| 6,309,349 | B1 | 10/2001 | Bertolero |
| 6,325,764 | B1 | 12/2001 | Griffith |
| 6,334,068 | B1 | 12/2001 | Hacker |
| 6,373,890 | B1 | 4/2002 | Freeman |
| 6,425,859 | B1 | 7/2002 | Foley |
| 6,450,952 | B1 | 9/2002 | Rioux |
| 6,466,817 | B1 | 10/2002 | Kaula |
| 6,473,639 | B1 | 10/2002 | Fischell |
| 6,500,128 | B2 | 12/2002 | Marino |
| 6,535,759 | B1 | 3/2003 | Epstein |
| 6,579,114 | B2 | 6/2003 | Lord |
| 6,609,018 | B2 | 8/2003 | Cory |
| 6,712,795 | B1 | 3/2004 | Cohen |
| 6,799,931 | B2 | 10/2004 | Kwilosz |
| 6,805,668 | B1 | 10/2004 | Cadwell |
| 6,837,716 | B1 | 1/2005 | Brazas |
| 6,847,849 | B2 | 1/2005 | Mamo |
| 6,851,430 | B2 | 2/2005 | Tsou |
| 6,869,301 | B2 | 3/2005 | Shimizu |
| 6,870,109 | B1 | 3/2005 | Villarreal |
| 6,926,728 | B2 | 8/2005 | Zucherman |
| 6,945,933 | B2 | 9/2005 | Branch |
| 7,072,521 | B1 | 7/2006 | Cadwell |
| 7,089,059 | B1 | 8/2006 | Pless |
| 7,104,965 | B1 | 9/2006 | Jiang |
| 7,177,677 | B2 | 2/2007 | Kaula |
| 7,214,197 | B2 | 5/2007 | Prass |
| 7,230,688 | B1 | 6/2007 | Villarreal |
| 7,261,688 | B2 | 8/2007 | Smith |
| 7,374,448 | B2 | 5/2008 | Jepsen |
| 7,470,236 | B1 | 12/2008 | Kelleher |
| 7,522,953 | B2 | 4/2009 | Kaula |
| 7,713,210 | B2 | 5/2010 | Byrd |
| 7,801,601 | B2 | 9/2010 | Maschino |
| 7,914,350 | B1 | 3/2011 | Bozich |
| 7,963,927 | B2 | 6/2011 | Kelleher |
| 7,983,761 | B2 | 7/2011 | Giuntoli |
| 8,108,039 | B2 * | 1/2012 | Saliga .................... A61B 5/369 600/546 |
| 8,147,421 | B2 | 4/2012 | Farquhar |
| 8,160,694 | B2 | 4/2012 | Salmon |
| 8,192,437 | B2 | 6/2012 | Simonson |

(56) References Cited

U.S. PATENT DOCUMENTS

| | | |
|---|---|---|
| D670,656 S | 11/2012 | Jepsen |
| 8,323,208 B2 | 12/2012 | Davis |
| 8,439,703 B2 | 5/2013 | Natoli |
| 8,876,813 B2 | 11/2014 | Min |
| 8,942,797 B2 | 1/2015 | Bartol |
| 8,958,869 B2 | 2/2015 | Kelleher |
| 9,084,551 B2 | 7/2015 | Brunnett |
| 9,138,586 B2 | 9/2015 | Eiger |
| 9,155,503 B2 | 10/2015 | Cadwell |
| 9,295,401 B2 | 3/2016 | Cadwell |
| 9,352,153 B2 | 5/2016 | Van Dijk |
| 9,730,634 B2 | 8/2017 | Cadwell |
| 10,238,467 B2 | 3/2019 | Cadwell |
| 2001/0049510 A1 | 12/2001 | Burr |
| 2002/0007188 A1 | 1/2002 | Arambula |
| 2002/0009916 A1 | 1/2002 | Lord |
| 2002/0088098 A1 | 7/2002 | Bouley |
| 2002/0095080 A1 | 7/2002 | Cory |
| 2003/0045808 A1 | 3/2003 | Kaula |
| 2003/0074033 A1 | 4/2003 | Pless |
| 2004/0030258 A1 | 2/2004 | Williams |
| 2004/0127810 A1 | 7/2004 | Sackellares |
| 2004/0192100 A1 | 9/2004 | Shimizu |
| 2005/0003682 A1 | 1/2005 | Brazas |
| 2005/0075578 A1 | 4/2005 | Gharib |
| 2005/0085743 A1 | 4/2005 | Hacker |
| 2005/0148927 A1 | 7/2005 | Ludin |
| 2005/0182454 A1 | 8/2005 | Gharib |
| 2005/0182456 A1 | 8/2005 | Ziobro |
| 2005/0277844 A1 | 12/2005 | Strother |
| 2006/0009754 A1 | 1/2006 | Boese |
| 2006/0085048 A1 | 4/2006 | Cory |
| 2006/0085049 A1 | 4/2006 | Cory |
| 2006/0122514 A1 | 6/2006 | Byrd |
| 2006/0135877 A1 | 6/2006 | Giftakis |
| 2006/0258951 A1 | 11/2006 | Bleich |
| 2006/0276720 A1 | 12/2006 | McGinnis |
| 2007/0016097 A1 | 1/2007 | Farquhar |
| 2007/0021682 A1 | 1/2007 | Gharib |
| 2007/0032841 A1 | 2/2007 | Urmey |
| 2007/0046471 A1 | 3/2007 | Nyalamadugu |
| 2007/0049962 A1 | 3/2007 | Marino |
| 2007/0184422 A1 | 8/2007 | Takahashi |
| 2007/0202005 A1 | 8/2007 | Maschke |
| 2008/0027507 A1 | 1/2008 | Bijelic |
| 2008/0058606 A1 | 3/2008 | Miles |
| 2008/0065144 A1 | 3/2008 | Marino |
| 2008/0071191 A1 | 3/2008 | Kelleher |
| 2008/0082136 A1 | 4/2008 | Gaudiani |
| 2008/0097164 A1 | 4/2008 | Miles |
| 2008/0108244 A1 | 5/2008 | Jepsen |
| 2008/0167574 A1 | 7/2008 | Farquhar |
| 2008/0183096 A1 | 7/2008 | Snyder |
| 2008/0194970 A1 | 8/2008 | Steers |
| 2008/0269777 A1 | 10/2008 | Appenrodt |
| 2008/0281313 A1 | 11/2008 | Fagin |
| 2008/0312520 A1 | 12/2008 | Rowlandson |
| 2009/0018399 A1 | 1/2009 | Martinelli |
| 2009/0043221 A1 | 2/2009 | Kaplan |
| 2009/0088660 A1 | 4/2009 | McMorrow |
| 2009/0105604 A1 | 4/2009 | Bertagnoli |
| 2009/0177112 A1 | 7/2009 | Gharib |
| 2009/0196471 A1 | 8/2009 | Goetz |
| 2009/0204016 A1 | 8/2009 | Gharib |
| 2009/0209879 A1 | 8/2009 | Kaula |
| 2009/0259108 A1 | 10/2009 | Miles |
| 2009/0279767 A1 | 11/2009 | Kukuk |
| 2010/0036384 A1 | 2/2010 | Gorek |
| 2010/0106011 A1 | 4/2010 | Byrd |
| 2010/0113898 A1 | 5/2010 | Kim |
| 2010/0152604 A1 | 6/2010 | Kaula |
| 2010/0168603 A1 | 7/2010 | Himes |
| 2010/0191305 A1 | 7/2010 | Imran |
| 2010/0249638 A1 | 9/2010 | Liley |
| 2010/0286554 A1 | 11/2010 | Davis |
| 2010/0317931 A1 | 12/2010 | Sarkela |
| 2010/0317989 A1 | 12/2010 | Gharib |
| 2011/0082383 A1 | 4/2011 | Cory |
| 2011/0184308 A1 | 7/2011 | Kaula |
| 2011/0295579 A1 | 12/2011 | Tang |
| 2011/0313530 A1 | 12/2011 | Gharib |
| 2012/0003862 A1 | 1/2012 | Newman |
| 2012/0046531 A1 | 2/2012 | Hua |
| 2012/0071779 A1 | 3/2012 | Sarkela |
| 2012/0109000 A1 | 5/2012 | Kaula |
| 2012/0109004 A1 | 5/2012 | Cadwell |
| 2012/0209082 A1 | 8/2012 | Al-Ali |
| 2012/0209346 A1 | 8/2012 | Bikson |
| 2012/0220891 A1 | 8/2012 | Kaula |
| 2012/0238855 A1 | 9/2012 | Lanning |
| 2012/0238893 A1 | 9/2012 | Farquhar |
| 2012/0265040 A1 | 10/2012 | Ito |
| 2012/0296230 A1 | 11/2012 | Davis |
| 2013/0012880 A1 | 1/2013 | Blomquist |
| 2013/0109996 A1 | 5/2013 | Turnbull |
| 2013/0138010 A1 | 5/2013 | Nierenberg |
| 2013/0152657 A1 | 6/2013 | Swinehart |
| 2013/0204315 A1 | 8/2013 | Wongsarnpigoon |
| 2013/0253447 A1 | 9/2013 | Ball |
| 2013/0304407 A1 | 11/2013 | George |
| 2014/0121555 A1 | 5/2014 | Scott |
| 2014/0275926 A1 | 9/2014 | Scott |
| 2014/0276181 A1 | 9/2014 | Sun |
| 2015/0150512 A1 | 6/2015 | Warner |
| 2015/0230749 A1 | 8/2015 | Gharib |
| 2015/0238106 A1 | 8/2015 | Lappalainen |
| 2015/0351643 A1 | 12/2015 | Edwards |
| 2015/0372433 A1 | 12/2015 | Lisogurski |
| 2016/0000382 A1 | 1/2016 | Jain |
| 2016/0174861 A1 | 6/2016 | Cadwell |
| 2016/0270679 A1 | 9/2016 | Mahon |
| 2016/0328991 A1 | 11/2016 | Simpson |
| 2017/0056663 A1 | 3/2017 | Kaemmerer |
| 2017/0100047 A1 | 4/2017 | Edwards |
| 2018/0117309 A1 | 5/2018 | Rapoport |
| 2018/0140829 A1 | 5/2018 | Ramos De Miguel, Sr. |
| 2018/0161123 A1 | 6/2018 | Cadwell |
| 2018/0198218 A1 | 7/2018 | Regan |
| 2018/0256097 A1 | 9/2018 | Bray |
| 2018/0296277 A1 | 10/2018 | Schwartz |
| 2019/0190187 A1 | 6/2019 | Fukazawa |
| 2020/0022603 A1 | 1/2020 | Cardenas |
| 2020/0108246 A1 | 4/2020 | Cadwell |
| 2020/0297282 A1 | 9/2020 | Batzer |
| 2020/0330772 A1 | 10/2020 | Hartmann-Bax |

FOREIGN PATENT DOCUMENTS

| | | |
|---|---|---|
| EP | 298268 | 1/1989 |
| EP | 0863719 A1 | 9/1998 |
| EP | 890341 | 1/1999 |
| EP | 972538 | 1/2000 |
| EP | 1182965 B1 | 3/2002 |
| EP | 2173238 A2 | 4/2010 |
| JP | H11513592 A | 11/1999 |
| JP | 2008546509 A | 12/2008 |
| WO | 2000038574 A1 | 7/2000 |
| WO | 2000066217 A1 | 11/2000 |
| WO | 2001037728 A1 | 5/2001 |
| WO | 2003005887 A2 | 1/2003 |
| WO | 2005030318 A1 | 4/2005 |
| WO | 2006042241 A2 | 4/2006 |
| WO | 2016028822 A1 | 2/2016 |
| WO | 2016105571 A1 | 6/2016 |

OTHER PUBLICATIONS

Clements, et al., "Evoked and Spontaneous Electromyography to Evaluate Lumbosacral Pedicle Screw Placement", 21 (5):600-604 (1996).

Danesh-Clough, et al., "The Use of Evoked EMG in Detecting Misplaced Thoracolumbar Pedicle Screws", 26(12):1313-1316 (2001).

(56) References Cited

OTHER PUBLICATIONS

Dezawa et al., "Retroperitoneal Laparoscopic Lateral Approach to the Lumbar Spine: A New Approach, Technique, and Clinical Trial", Journal of Spinal Disorders 13(2):138-143 (2000).
Dickman, et al., "Techniques in Neurosurgery", National Library of Medicine, 3 (4) 301-307 (1997).
Epstein, et al., "Evaluation of Intraoperative Somatosensory-Evoked Potential Monitoring During 100 Cervical Operations", 18(6):737-747 (1993), J.B. Lippincott Company.
Glassman, et al., "A Prospective Analysis of Intraoperative Electromyographic Monitoring of Pedicle Screw Placement with Computed Tomographic Scan Confirmation", 20(12):1375-1379.
Goldstein, et al., "Minimally Invasive Endoscopic Surgery of the Lumbar Spine", Operative Techniques in Orthopaedics, 7 (1):27-35 (1997).
Greenblatt, et al., "Needle Nerve Stimulator-Locator", 41 (5):599-602 (1962).
H.M. Mayer, "Minimally Invasive Spine Surgery, A Surgical Manual", Chapter 12, pp. 117-131 (2000).
Hinrichs, et al., "A trend-detection algorithm for intraoperative EEG monitoring", Med. Eng. Phys. 18 (8):626-631 (1996).
Bergey et al., "Endoscopic Lateral Transpsoas Approach to the Lumbar Spine", SPINE 29 (15):1681-1688 (2004).
Holland, "Spine Update, Intraoperative Electromyography During Thoracolumbar Spinal Surgery", 23 (17):1915-1922 (1998).
Holland, et al., "Continuous Electromyographic Monitoring to Detect Nerve Root Injury During Thoracolumbar Scoliosis Surgery", 22 (21):2547-2550 (1997), Lippincott-Raven Publishers.
Hovey, A Guide to Motor Nerve Monitoring, pp. Mar. 1-31, 20, 1998, The Magstim Company Limited.
Kevin T. Foley, et al., "Microendoscipic Discectomy" Techniques in Neurosurgery, 3:(4):301-307, © 1997 Lippincott-Raven Publishers, Philadelphia.
Kossmann et al., "The use of a retractor system (SynFrame) for open, minimal invasive reconstruction of the anterior column of the thoracic and lumbar spine", 10:396-402 (2001).
Kossmann, et al., "Minimally Invasive Vertebral Replacement with Cages in Thoracic and Lumbar Spine", European Journal of Trauma, 2001, No. 6, pp. 292-300.
Lenke, et al., "Triggered Electromyographic Threshold for Accuracy of Pedicle Screw Placement, An Animal Model and Clinical Correlation", 20 (14):1585-1591 (1995).
Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.
Maguire, et al., "Evaluation of Intrapedicular Screw Position Using Intraoperative Evoked Electromyography", 20 (9):1068-1074 (1995).
Mathews et al., "Laparoscopic Discectomy With Anterior Lumbar Interbody Fusion, A Preliminary Review", 20 (16):1797-1802, (1995), Lippincott-Raven Publishers.
Bertagnoli, et al., "The AnteroLateral transPsoatic Approach (ALPA), A New Technique for Implanting Prosthetic Disc-Nucleus Devices", 16 (4):398-404 (2003).
Michael R. Isley, et al., "Recent Advances in Intraoperative Neuromonitoring of Spinal Cord Function: Pedicle Screw Stimulation Techniques", Am. J. End Technol. 37:93-126 (1997).
Minahan, et al., "The Effect of Neuromuscular Blockade on Pedicle Screw Stimulation Thresholds" 25(19):2526-2530 (2000).
Pimenta et al., "Implante de protese de nucleo pulposo: analise inicial", J Bras Neurocirurg 12 (2):93-96, (2001).
Raymond J. Gardocki, MD, "Tubular diskectomy minimizes collateral damage", AAOS Now, Sep. 2009 Issue, http://www.aaos.org/news/aaosnow/sep09/clinical12.asp.
Raymond, et al., "The NerveSeeker: A System for Automated Nerve Localization", Regional Anesthesia 17:151-162 (1992).
Reidy, et al., "Evaluation of electromyographic monitoring during insertion of thoracic pedicle screws", British Editorial Society of Bone and Joint Surgery 83 (7):1009-1014, (2001).

Rose et al., "Persistently Electrified Pedicle Stimulation Instruments in Spinal Instrumentation: Technique and Protocol Development", Spine: 22(3): 334-343 (1997).
Teresa Riordan "Patents; A businessman invents a device to give laparoscopic surgeons a better view of their worK", New York Times www.nytimes.com/2004/29/business/patents-businessman-invents-device-give-la (Mar. 2004).
Toleikis, et al., "The usefulness of Electrical Stimulation for Assessing Pedicle Screw Placements", Journal of Spinal Disorders, 13 (4):283-289 (2000).
U.Schick, et al., "Microendoscipic lumbar discectomy versus open surgery: an intraoperative EMG study", pp. 20-26, Published online: Jul. 31, 2001 © Springer-Verlag 2001.
Bose, et al., "Neurophysiologic Monitoring of Spinal Nerve Root Function During Instrumented Posterior Lumbar Spine Surgery", 27 (13):1440-1450 (2002).
Vaccaro, et al., "Principles and Practice of Spine Surgery", Mosby, Inc. © 2003, Chapter 21, pp. 275-281.
Vincent C. Traynelis, "Spinal arthroplasty", Neurosurg Focus 13 (2):1-7. Article 10, (2002).
Welch, et al., "Evaluation with evoked and spontaneous electromyography during lumbar instrumentation: a prospective study", J Neurosurg 87:397-402, (1997).
Zouridakis, et al., "A Concise Guide to Intraoperative Monitoring", Library of Congress card No. 00-046750, Chapters, p. 21, chapter 4, p. 58 and chapter 7 pp. 119-120.
Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.
Chapter 9, "Root Finding and Nonlinear Sets of Equations", Chapter 9:350-354, http://www.nr.com.
Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".
Ford et al., Electrical characteristics of peripheral nerve stimulators, implications for nerve localization, Dept. of Anesthesia, University of Cincinnati College of Medicine, Cincinnati, OH 45267, pp. 73-77.
Deletis et al., "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.
Urmey "Using the nerve stimulator for peripheral or plexus nerve blocks" Minerva Anesthesiology 2006; 72:467-71.
Butterworth et al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.
Calancie, et al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).
Calancie, et al., "Threshold-level repetitive transcranial electrical stimulation for intraoperative monitoring of central motor conduction", J. Neurosurg 95:161-168 (2001).
Calancie, et al., Stimulus-Evoked EMG Monitoring During Transpedicular Lumbosacral Spine Instrumentation, Initial Clinical Results, 19 (24):2780-2786 (1994).
Carl T. Brighton, "Clinical Orthopaedics and Related Research", Clinical Orthopaedics and related research No. 384, pp. 82-100 (2001).
International Search Report for PCT/US2019/063793, dated Feb. 19, 2020.
International Search Report for PCT/US2017/062559, dated Jan. 26, 2018.
Brainstorm Website, http://neuroimage.usc.edu/brainstorm/ accessed online Oct. 9, 2021, available online Apr. 11, 2018. (Year: 2018).
Compumedics Website, "Compumedics Profusion EEG 4" accessed online Oct. 9, 2021, available online Feb. 23, 2017 (ttps://www.

(56) References Cited

OTHER PUBLICATIONS compumedics.com.au/wp-content/uploads/2016/08/AD125-02-Profusion-EEG4-brochureLR.pdf (Year:2017).

Intelimed Website, "Compumedics Profusion EEG 5 Top Features" accessed online Oct. 9, 2021, available online Sep. 30, 2014 2014).

Deff Corporation, No more confusion about which direction to plug in. A USB cable that can be plugged in both ways is now available. A connector is equipped with an LED indicator to check a charging status of a smartphone. Nov. 6, 2015 (Dec. 28, 2021 Search) Internet URL:https://deff.co.jp/news/dca-mbled (Document showing known technology).

"Long, S; "Phase Locked Loop Circuits", Apr. 27, 2005". (Year: 2005).

Brainstorm website, https://web.archive.org/web/20180421074035/https://neuroimage.usc.edu/brainstorm/Tutorials/MontageEditor, available online Apr. 21, 2018 (Year: 2018).

Brainstorm website, https://web.archive.org/web/20180330235454/http://neuroimage.usc.edu/brainstorm/Tutorials/CreateProtocol,) available on Mar. 30, 2018 (Year: 2018).

Brainstorm website,https://web.archive.org/web/20180416072211/http://neuroimage.usc.edu/brainstorm/Screenshots ,available on Apr. 16, 2018 (Year: 2018).

Brainstorm website,https://web.archive.org/web/20180411211909/https://neuroimage.usc.edu/brainstorm/Introduction,available on Apr. 11, 2018 (Year: 2018).

Brainstorm website,https://web.archive.org/web/20180505021718/https://neuroimage.usc.edu/brainstorm/Tutorials/Epileptogenicity, available on May 5, 2018 (Year: 2018).

\* cited by examiner

US 11,596,337 B2

METHODS AND SYSTEMS FOR OPERATING AN INTRAOPERATIVE NEUROPHYSIOLOGICAL MONITORING SYSTEM IN CONJUNCTION WITH ELECTROCAUTERY PROCEDURES

CROSS-REFERENCE

The present application relies on U.S. Provisional Patent Application No. 62/772,753, entitled "Methods for Operating an Intraoperative Neurophysiological Monitoring System in Conjunction with Electrocautery Procedures" and filed on Nov. 29, 2018, and U.S. Provisional Patent Application No. 62/662,138, of the same title and filed on Apr. 24, 2018, for priority, both of which are herein incorporated by reference in their entirety.

FIELD

The present specification generally relates to intraoperative neurophysiological monitoring (IONM) systems, and more specifically to methods for determining high frequency noise and/or manipulating input signals during an electrocautery procedure being performed on a patient being monitored by an IONM system.

BACKGROUND

Intraoperative neurophysiological monitoring (IONM) refers to the use of electrophysiological methods such as electroencephalography (EEG), electromyography (EMG), and evoked potentials to monitor the functional integrity of certain neural structures (e.g., nerves, spinal cord and parts of the brain) during surgery. Electrocautery equipment usage during surgery can result in interference with various signals monitored by an intraoperative neurophysiological monitoring (IONM) system. This may lead to distortion of patient signal waveforms, resulting in invalid data being presented and/or stored in the IONM system. In some cases, this may also cause recording device channels to saturate. Hence, there is a need for a noise detection system that can determine whether the incoming patient signals should be processed as usual or ignored by the IONM system, depending on the presence of interference from electrocautery equipment or noise from another source. There is also need for a noise detection system that can restore data acquisition when noise is no longer present in the system.

Some conventional noise interference detection techniques primarily consist of hardware solutions that are tailored to detect specific noise frequency ranges from an electrosurgical unit (ESU). These hardware solutions, however, do not address possible erroneous detection of artifacts other than ESU signals such as electrical stimulation waveforms on the patient. Hence, there is a need for a hardware solution that is tailored to detect the specific noise frequency range generated by an ESU and also configured to ignore other high frequency and low occurrence artifacts such as electrical stimulation waveforms on the patient.

Other existing solutions may include monitoring a recording device channel for noise or saturation. Similarly, for certain applications, there exist solutions where the data is processed in a manner that aims to digitally remove interference from patient signals. Both of these methods require analyzing data from the patient signals. In situations where the acquisition system is severely impacted by the interference to the point where the data is unreliable, there is a need for a method which does not solely rely on patient signals to determine interference.

In applications where the noise interference can be generated by sources other than ESU activity, there is a need for a noise interference detection method that can be adapted to detect a wide range of noise sources rather than being specific to ESU interference by using detection parameters that are configurable based on the noise interference being detected.

In addition, in cases where an electrocautery procedure is in progress during IONM, a charge can build up on the electrodes connected to the patient. If the affected channels' hardware gain is high enough and hardware high-pass filter cutoff is low enough, this charge accumulation can cause a saturation state which can persist for up to several minutes after electrocautery has finished. This saturation state renders the EEG data unusable immediately following electrocautery activity. This problem is common for inputs used in EEG data acquisition.

U.S. Pat. No. 8,961,505, assigned to Medtronic, Inc., discloses "[a] device comprising: a plurality of electrodes configured to acquire an electrical signal in a patient; and a detection module configured to: determine whether the acquired electrical signal includes signal content greater than a threshold amount in each of N different frequency bands, wherein N is an integer that is greater than 1; and detect operation of an electrosurgical device on the patient based on how many of the N different frequency bands include signal content greater than the threshold amount."

U.S. Pat. No. 8,108,039, assigned to Neurowave Systems, Inc., discloses "[a] method of acquiring biopotential signals from a subject in the presence of electrical interference comprising the steps of: attaching at least 2 electrodes to a subject, acquiring and filtering biopotential signals from the subject using amplification circuitry, with said circuitry comprising: at least one input filter for high frequency (HF) electrical interference rejection, and an isolation barrier; obtaining a quantitative measure of the level of HF electrical interference, and transmitting the biopotential signals and measured HF electrical interference level to a processor, wherein electrical interference consisting of frequencies 20 kHz or above is removed."

U.S. Pat. No. 9,439,601, assigned to Neurowave Systems, Inc., discloses "[a] method of acquiring signals from a subject in the presence of high frequency (HF) electrical interference comprising the steps of: attaching at least 2 electrodes to a subject; acquiring signals from the subject using circuitry for rejection of HF electrical interference, with said circuitry comprising: at least one active input filter, and an isolation barrier where data is transmitted; measuring the level of remaining HF electrical interference across said isolation barrier; and transmitting the signals and measured interference level to a processor, wherein said processor uses said measure of HF electrical interference to modify at least one behavior of the at least one active input filter."

PCT Publication Number WO2017010556162, assigned to Draeger Medical Systems, Inc., describes circuits for detecting an electrosurgical unit signal, wherein "[a]n example circuit includes: a filter configured to process a floating ground signal associated with measuring a bio potential signal of a patient, and a detector configured to output a sensing signal based at least in part on the floating grounding and the Earth ground for detecting an electrosurgical unit signal."

Within an IONM system, the hardware gain on an input is commonly chosen to be as high as possible for a given data type in order to acquire data with the highest resolution possible. The high-pass filter cutoff is typically chosen to be as low as possible to keep relevant frequencies while still blocking DC. One possible solution to bring a channel out of saturation is to lower the hardware gain which increases the signal range for that channel. However, manually changing the channel hardware gain is cumbersome and requires the user to know that the data is saturated, which is not always obvious after it has passed through the software filtering process. Hence, there is need for a method of decreasing the hardware gain to eliminate a saturated state by increasing the signal range. There is also need for a method of returning the hardware gain to an original level when the inputs are no longer saturated. There is a need for a method of automatically adjusting the hardware gain while in the saturated state and keeping the data usable with no intervention required from a user, thereby improving quality of data and user experience. In making these hardware gain adjustments, it can be helpful to know if ESU interference is occurring or has just occurred on the patient signal. This information can be provided by either of the noise interference detection methods previously described.

SUMMARY

The following embodiments and aspects thereof are described and illustrated in conjunction with systems, tools and methods, which are meant to be exemplary and illustrative, not limiting in scope.

The present specification discloses a method for detecting a high frequency noise causing interference on patient signals being monitored by an IONM system using a primarily hardware solution. This method includes configuration to ignore unwanted high frequency and low occurrence artifact such as electrical stimulation waveforms on the patient. This additional benefit prevents these artifacts from triggering a false positive detection of the noise interference of interest.

The present specification discloses a system for detecting noise causing interference with signals being monitored by an intraoperative neurophysiological monitoring (IONM) system in electrical communication with a patient, said noise being characterized by frequencies greater than 100 kHz, the system for detecting high frequency noise comprising: a first circuit comprising an isolated ground plane electrically coupled, through the patient, to an electrosurgical unit in electrical communication with the patient; and a second circuit comprising a microcontroller, a first signal processing path and a second signal processing path, wherein a portion of the second circuit is positioned over the first circuit such that, during operation, a capacitance is formed between the first circuit and the second circuit and wherein the system is configured to use the first signal processing path or the second signal processing path to detect said noise causing interference.

Optionally, the portion of the second circuit comprises a copper pad.

Optionally, the system further comprises a microcontroller, wherein the microcontroller comprises a first analog to digital converter configured to receive signals from the first signal processing path.

Optionally, the second signal processing path comprises a high pass filter. Optionally, the microcontroller comprises a second analog to digital converter configured to receive signals from the second signal processing path.

Optionally, the first signal processing path comprises an N pole high pass filter configured to remove unwanted low frequency signals below a predetermined threshold value and generate a filtered signal, wherein the low frequency signals comprise signals having a frequency of 100 kHz or less.

Optionally, the first signal processing path comprises a hardware gain circuit configured to apply a gain to a filtered signal.

Optionally, the first signal processing path comprises a rectifier circuit configured to rectify a filtered signal for direct current voltage.

Optionally, the first signal processing path comprises a delay circuit configured to not be charged by electrical signals having frequencies greater than 100 kHz and rate of occurrence of less than or equal to 200 Hz. Optionally, the delay circuit is configured to be charged by electrical signals having frequencies greater than 100 kHz and rate of occurrence of greater than or equal to 30 kHz.

Optionally, the first signal processing path comprises a low pass filter configured to remove said noise from direct current voltage.

Optionally, the second signal processing path is configured to sample signals transmitted by the first circuit and run said sample signals through an exponentially weighted variance function.

Optionally, the first signal processing path is configured to provide a direct current voltage with a threshold to determine activity of the electrosurgical unit.

The present specification also discloses a circuit for use in a system for detecting noise causing interference on patient signals being monitored by an intraoperative neurophysiological monitoring (IONM) system, said noise having frequencies greater than 100 kHz and rate of occurrence greater than 30 kHz, the circuit comprising: a first filter configured to remove predefined low frequency signals to generate a filtered signal, wherein the low frequency signals comprise signals having a frequency less than 100 kHz; a gain circuit configured to apply gain to the filtered signal and generate an amplified signal; a rectifier circuit configured to rectify the amplified signal and generate a direct current voltage; a delay circuit configured to attenuate the direct current voltage for contribution from periodic signals with frequencies greater than 100 kHz and rate of occurrence of less than or equal to 200 Hz; and a second filter configured to remove said noise from the direct current voltage; wherein the circuit is further configured to apply a threshold to the direct current voltage and determine activity of an electrosurgical unit in electrical communication with the patient.

Optionally, the circuit for use in a system for detecting noise causing interference on patient signals being monitored by an IONM system further comprises a transient voltage suppression diode configured to provide transient protection of circuit components with absolute voltage limit.

Optionally, the delay circuit is configured to be charged by electrical signals having frequencies greater than 100 kHz and rate of occurrence of 30 kHz or more.

The present specification also discloses a method for detecting noise causing interference on patient signals being monitored by an intraoperative neurophysiological monitoring (IONM), wherein the method is implemented using a non-isolated circuit that receives a signal from an isolated circuit, said non-isolated circuit comprising a microcontroller having an analog to digital converter, a diode, a first filter, a gain circuit, a rectifier circuit, a delay circuit, and a second filter, the method comprising: using the diode to protect the non-isolated circuit from electrical transients; filtering the signal using the first filter to attenuate low frequencies in the signal and output a filtered signal, wherein the low frequency signals comprise signals having a frequency of 100 kHz or less; amplifying the filtered signal by a predefined gain using the gain circuit and generating a gained signal; rectifying the gained signal using the rectifier circuit and generating a rectified signal; delaying the rectified signal with the delay circuit; filtering said noise from the signal with the second filter, wherein said noise is characterized by frequencies greater than 100 kHz and rate of occurrence of greater than or equal to 30 kHz; and inputting a signal resulting from the second filter into the analog to digital converter on the microcontroller.

Optionally, the delay circuit is configured to not be charged by signals having frequencies greater than 100 kHz and rate of occurrence of 200 Hz or less.

Optionally, the delay circuit is configured to be charged by signals having frequencies greater than 100 kHz and rate of occurrence of 30 kHz or more.

The present specification also discloses a method for detecting noise causing interference on patient signals being monitored by an intraoperative neurophysiological monitoring (IONM) system, said noise being attributed to an electrosurgical unit in electrical communication with a patient, the method comprising: capacitively coupling signals from an isolated circuit to a non-isolated circuit; rectifying the coupled signals to generate rectified signals; sampling the rectified signals using a processor for detecting a direct current value of the rectified signals; and indicating detection of said noise if the detected direct current value exceeds a predefined threshold value.

Optionally, the signals are capacitively coupled by positioning a portion of the non-isolated circuit over the isolated circuit, and wherein said portion comprises a copper pad.

Optionally, the method further comprises routing said coupled signals through a single pole high-pass filter.

Optionally, the method further comprises routing said coupled signals through a multiple pole high-pass filters.

Optionally, the method further comprises amplifying the coupled signals by a gain of 1 or more.

Optionally, the coupled signals are rectified using a rectifier circuit.

Optionally, the rectified signals are delayed by using a circuit comprising a capacitor and a resistor.

Optionally, the rectified signals from the isolated ground plane are routed through a low pass filter.

Optionally, the method further comprises routing the rectified signals to an analog to digital converter using a microcontroller in the non-isolated circuit.

Optionally, detecting said noise comprises causing an alarm status to be set to a true state. Optionally, the alarm status is set to the true state when the direct current value remains above the predefined threshold value for a predefined period of time.

Optionally, the method further comprises setting an alarm status to a false state if the detected direct current value does not exceed the predefined threshold value.

The present specification also discloses a method for detecting signal saturation in an intraoperative neurophysiological monitoring (IONM) system, the method comprising: analyzing data from each of a plurality of referential input signals of the IONM system, wherein each of the plurality of referential input signals have a first gain value, and wherein the data is grouped in predefined segments; detecting a segment saturation for each of the plurality of referential input signals, if the data within each predefined segment has a same positive or negative sign, and the data within each predefined segment is above a predefined threshold value; detecting a global saturation value for each of the plurality of referential input signals, if each of the plurality of referential input signals has at least been in segment saturation for a predefined period of time with the same positive or negative sign; re-setting a segment saturation state and a global saturation state to a false state for each of the plurality of referential input signals if any discontinuous data is detected within any of the predefined segments; decreasing a gain value for all of the plurality of referential input signals if any of the plurality of input signals is in a global saturation state; and re-setting the gain value of each of the plurality of referential input signals to the first gain value when all of the plurality of referential input signals have a false global saturation state.

Optionally, the method further comprises monitoring for each of the plurality of referential input signals, a sign and an amplitude of the data in the predefined segments.

Optionally, the method further comprises filtering the data from each of the plurality of referential input signals using a high-pass filter for removing any direct current offset.

Optionally, the method further comprises ignoring the data from each of the plurality of referential input signals until all of the plurality of referential input signals have a false global saturation state.

Optionally, each of the plurality of referential input signals have a same high-pass filter cutoff when the IONM system is being used for an electroencephalography procedure.

Optionally, a saturation of the plurality of referential input signals is caused by an electrocautery process being performed on a patient being monitored by the IONM system.

Optionally, a saturation of the plurality of referential input signals is caused by a source other than an electrocautery process being performed on the patient being monitored by the IONM system.

Optionally, the method further comprises enabling said signal saturation detection for ESU activity.

Optionally, the method further comprises enabling signal saturation detection during all data acquisition.

The present specification also discloses a method for detecting noise in input patient signals being monitored by an intraoperative neurophysiological monitoring (IONM) system, the method comprising: capacitively coupling signals from an isolated circuit to a non-isolated sampling the coupled signal using a processor; determining a variance value of each sampled signal by a detector function; and indicating detection of said noise if the variance value exceeds a predefined threshold value.

Optionally, said capacitive coupling is enabled by positioning a copper pad of the non-isolated circuit over an isolated ground plane of the isolated circuit.

Optionally, the method further comprises routing the coupled signals through a high-pass filter to an analog to digital converter.

Optionally, an alarm is not activated if the variance value does not exceed the predefined threshold value.

Optionally, an alarm is activated if the variance value exceeds the threshold value.

Optionally, the detection is processed within a firmware of the IONM in order to decrease latency in detection of said noise.

Optionally, the method further comprises removing outlier data from the sampled signal.

Optionally, determining the variance value of each sampled signal comprises determining a weighted variance value of the signal by the IONM system firmware.

Optionally, the weighted variance value is exponentially weighted.

The present specification also discloses a system for detecting a high frequency noise causing interference on patient signals being monitored by an IONM system, the system for detecting high frequency noise comprising: at least one electrosurgical unit in electrical connection with a patient; a first circuit comprising an isolated ground plane in electrical connection with the electrosurgical unit through the patient; and a second circuit comprising a microcontroller, a first signal processing path, and a second signal processing path, wherein a copper pad of the second circuit is positioned over said first circuit to form capacitance between the first circuit and the second circuit; wherein the system is configured to use the first signal processing path or the second signal processing path to detect a high frequency noise causing interference and wherein the first signal processing path is configured to detect high frequency noise with less software computation than the second signal processing path and the second signal processing path comprises fewer components than the first signal processing path.

Optionally, the microcontroller comprises a first ADC pin configured to receive signals from the first signal processing path. Optionally, the second signal processing path comprises a high pass filter and the microcontroller comprises a second ADC pin configured to receive signals from the second signal processing path.

Optionally, the first signal processing path comprises an N pole high pass filter configured to remove unwanted low frequency signals. Optionally, the first signal processing path comprises a hardware gain circuit configured to apply hardware gain to a filtered signal. Optionally, the first signal processing path comprises a rectifier circuit configured to rectify a filtered signal for DC voltage and the first signal processing path comprises a delay circuit configured to attenuate contribution from periodic signals with high frequency content and low frequency occurrence. Optionally, the delay circuit is configured to not be charged by electrical signals having frequency content greater than 100 kHz and occurrence frequencies of less than or equal to 200 Hz. Optionally, the delay circuit is configured to be charged by electrical signals having frequency content greater than 100 kHz and occurrence frequencies of greater than or equal to 30 kHz.

Optionally, the first signal processing path comprises a low pass filter configured to remove high frequency noise from DC voltage and the second signal processing path is configured to sample signals transmitted by the first circuit at a high frequency to determine frequency content and/or variance. Optionally, the first signal processing path is configured to provide a DC voltage with a threshold to determine ESU activity.

The present specification also discloses a circuit for use in a system for detecting a high frequency noise causing interference on patient signals being monitored by an IONM system, the circuit comprising: an N pole high pass filter configured to remove unwanted low frequency signals; a gain circuit configured to apply gain to a filtered signal; a rectifier circuit configured to rectify a filtered signal for DC voltage; a delay circuit configured to attenuate contribution from periodic signals with high frequency content and low frequency occurrence; and a low pass filter configured to remove high frequency noise from DC voltage; wherein the circuit is configured to provide a DC voltage with a threshold to determine ESU activity indicative of high frequency noise.

Optionally, the circuit for use in a system for detecting a high frequency noise causing interference on patient signals being monitored by an IONM system further comprises a transient voltage suppression diode configured to provide transient protection of circuit components with absolute voltage limit. Optionally, the delay circuit is configured to not be charged by electrical signals having frequency content greater than 100 kHz and occurrence frequencies of less than or equal to 200 Hz. Optionally, the delay circuit is configured to be charged by electrical signals having frequency content greater than 100 kHz and occurrence frequencies of greater than or equal to 30 kHz.

The present specification also discloses a method for detecting a high frequency noise causing interference on patient signals being monitored by an IONM system, wherein the system includes a circuit comprising a microcontroller having an ADC pin, a transient voltage suppression diode, an N pole high pass filter, a gain circuit, a rectifier circuit, a delay circuit, and a low pass filter, the method comprising: using the transient voltage suppression diode to protect the circuit components from transients; filtering a routed signal with the N pole high pass filter to attenuate low frequency signals; amplifying the signal by a hardware gain of 'A' with the gain circuit; rectifying the signal with the rectifier circuit; delaying the rectified signal with the delay circuit to attenuate contribution from periodic signals with high frequency content and low frequency occurrence; filtering unwanted high frequency noise from the signal with the low pass filter; and inputting the signal into the ADC pin on the microcontroller.

Optionally, the delay circuit is configured to not be charged by electrical signals having frequency content greater than 100 kHz and occurrence frequencies of less than or equal to 200 Hz. In an embodiment, the delay circuit is configured to be charged by electrical signals having frequency content greater than 100 kHz and occurrence frequencies of greater than or equal to 30 kHz.

The present specification also discloses a method for detecting a high frequency noise causing interference on patient signals being monitored by an IONM system, the method comprising: adding a non-isolated copper pour over an isolated ground plane in a recording device circuitry of the IONM system to capacitively couple signals from the isolated ground plane to the copper pour; processing and rectifying the signals from the isolated ground plane coupled with the copper pour by using hardware components; sampling the rectified signals with a processor for detecting a DC threshold value of the processed and rectified signals; and indicating detection of noise interference on patient signals being monitored by an IONM system if the detected DC threshold value exceeds a predefined threshold value.

Optionally, the method further comprises routing signals from the isolated ground plane to the copper pour through a single or multiple pole hardware high-pass filter.

Optionally, the method further comprises amplifying the isolated ground signal by a gain of 1 or more.

Optionally, the signals from the isolated ground plane are rectified using a rectifier circuit.

Optionally, the rectified signals from the isolated ground plane are delayed by using a capacitor/resistor circuit.

Optionally, the rectified signals from the isolated ground plane are routed through a low pass filter.

Optionally, the method further comprises routing the rectified signals from the isolated ground plane signal to an ADC pin on a processor of the IONM system.

Optionally, detecting noise interference on patient signals comprises causing an alarm status to be set to "true".

Optionally, the alarm status is set to "true" until the DC threshold value remains below the predefined threshold value for a predefined period of time.

Optionally, the method further comprises setting an alarm status to "false" if the detected DC threshold value does not exceed the predefined threshold value.

The present specification also discloses a method for detecting signal saturation in an IONM system, the method comprising: analyzing incoming data from each of a plurality of referential input signals of the IONM system, wherein all of the said referential input signals share the same original hardware gain value, and wherein the incoming data is grouped in predefined segments; detecting a segment saturation for each of the plurality of referential input signals, if the data within each segment has the same sign, and the data within each segment is above a predefined threshold value; detecting a global saturation value for each referential input signal, if the input signal has been in segment saturation for a predefined period of time with the same sign; re-setting the segment saturation state and the global state to "false" for each referential input signal if any discontinuous data is detected within any of the data segments; decreasing the hardware gain value for all of the referential input signals if any of the input signal is in a global saturation state; and re-setting the hardware gain of each of the referential input signals to the original hardware gain value when all of the input signals have a "false" global saturation state.

Optionally, the method further comprises monitoring for each of the input signals, a sign and an amplitude of the data for successive data segments.

Optionally, the method further comprises filtering using a high-pass software filter the incoming data from each of the referential input signals for removing any DC offset.

Optionally, the method further comprises ignoring the incoming data from each of the referential input signals until all of the input signals have a "false" global saturation state.

Optionally, the input signals have the same low high-pass filter cutoff when the IONM system is being used for an EEG procedure.

Optionally, the signal saturation is caused due to an electrocautery process being performed on a patient being monitored by the IONM system.

Optionally, the method further comprises ignoring saturation of the input signals if ESU activity has not been detected within a recent window of time.

Optionally, the signal saturation is caused due to a source other than an electrocautery process being performed on the patient being monitored by the IONM system.

Optionally, saturation detection is only enabled for ESU activity or if ESU activity has recently finished.

Optionally, saturation detection is enabled during all data acquisition.

The present specification also discloses a method for detecting a high frequency noise causing interference on patient signals being monitored by an IONM system using minimal hardware components. This method provides greater flexibility for detecting a wide range of noise sources and is not limited to detecting noise generated by an ESU.

The present specification also discloses a method for detecting a noise interference in input patient signals being monitored by an IONM system, the method comprising: adding a non-isolated copper pour over an isolated ground plane in a recording device board of the IONM system to capacitively couple signals from the isolated ground plane to the copper pour routing an isolated ground plane signal; sampling the signal from the copper pour with a processor; determining a variance value of each sampled signal by a detector function; and indicating detection of a noise interference if the variance value exceeds a predefined threshold value.

Optionally, the method further comprises routing an isolated ground detector signal from a recording device through a hardware high-pass filter to an ADC pin.

Optionally, interference detection is indicated by causing an alarm status to be set to "true".

Optionally, the alarm status is set to "false" if the variance value does not exceed the predefined threshold value.

Optionally, the alarm status is set to "true" until the variance value remains below the threshold value for a predefined period of time.

Optionally, the detector function is processed within a firmware of the IONM in order to minimize the latency in detection of a noise interference event.

Optionally, the method further comprises removing outlier data from the sampled signal.

Optionally, the routed signal is a capacitively coupled signal between isolated ground and non-isolated ground.

Optionally, determining a variance value of each sampled signal by a detector function comprises determining an exponentially weighted variance value of the signal by the IONM system firmware.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein.

DETAILED DESCRIPTION

Figure 1:
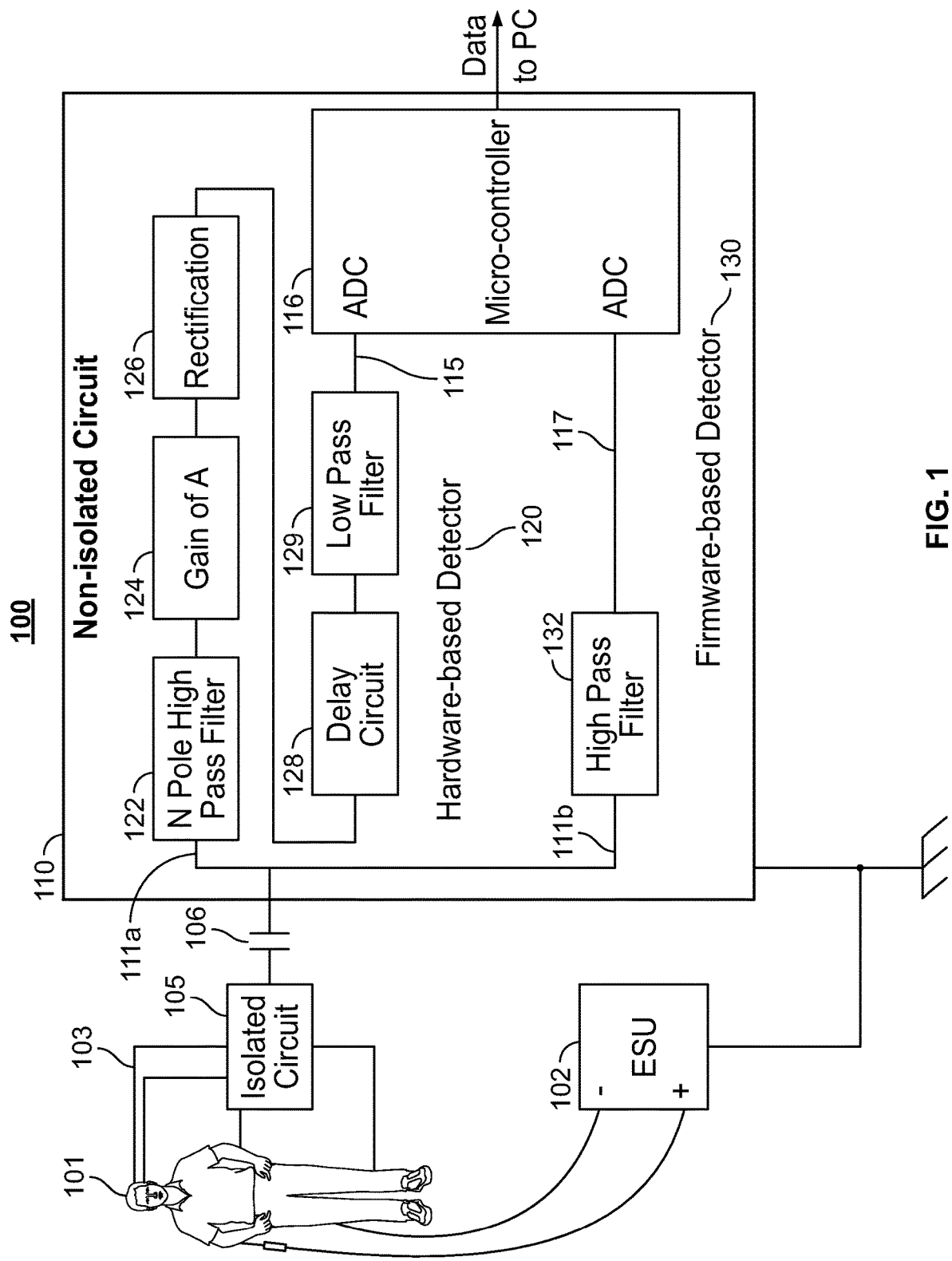
FIG. 1 is a block diagram of a system for detecting high frequency noise interference when a surgical procedure is being performed on a patient being monitored by an IONM system, in accordance with some embodiments of the present specification.

Electrocautery may result in high frequency noise interference in patient electrode signals for intraoperative neurophysiological monitoring. The present specification describes methods for determining high frequency noise causing interference in patient signals when a surgical procedure is being performed, using an ESU, on the patient being monitored by an IONM system. In an embodiment, the present specification provides a high frequency noise detector that allows interference on patient signals being monitored by an IONM system to be detected from non-isolated circuitry of the system, which provides a low latency status report to the IONM system. This noise detection status information can be used to decide how to process incoming data into the system.

This present specification provides a primarily hardware-based solution and an alternative primarily firmware-based solution. The primarily hardware-based detector of the present specification includes a delay circuit to prevent unwanted detection of high frequency and low occurrence artifacts such as electrical stimulator waveforms. The primarily firmware-based detector of the present specification uses a configurable variance threshold for noise detection to adapt to varying environments.

In another embodiment, the present specification provides an integrated electrocautery detection system to determine that an electrocautery device is in use during an IONM process and provides a method for adjusting referential input gain to alleviate saturation caused by electrocautery noise, during or immediately after an electrocautery device is used in conjunction with an IONM system. While in this state, or shortly thereafter, if the referential input hardware gain is at the highest level and the high-pass filter cutoff is at its lowest level, the present specification provides a method for continuously monitoring said input signals to determine their saturation state and adjusting the input hardware gain for all referential inputs to the next lower setting, if any of the input signals are deemed to be saturated, as saturation renders the signal data unusable. After the hardware gain adjustment, the input signals are continuously analyzed to determine if they would be saturated if the input hardware gain were returned to a high value. If not, then the hardware gain is adjusted to a high value, wherein the data resolution is increased. In an embodiment, hardware gain adjustment decisions are implemented by using two hardware gain levels and a set of algorithms within an IONM system.

In another embodiment, the present specification provides a method for adjusting referential input gain to alleviate saturation caused by interference from a source other than an electrocautery device.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

It should be noted herein that any feature or component described in association with a specific embodiment may be used and implemented with any other embodiment unless clearly indicated otherwise.

A "computing device" is at least one of a cellular phone, PDA, smart phone, tablet computing device, patient monitor, custom kiosk, or other computing device capable of executing programmatic instructions. It should further be appreciated that each device and monitoring system may have wireless and wired receivers and transmitters capable of receiving and transmitting data. Each "computing device" may be coupled to at least one display, which displays information about the patient parameters and the functioning of the system, by means of a GUI. The GUI also presents various menus that allow users to configure settings according to their requirements. The system further comprises at least one processor (not shown) to control the operation of the entire system and its components. It should further be appreciated that the at least one processor is capable of processing programmatic instructions, has a memory capable of storing programmatic instructions, and employs software comprised of a plurality of programmatic instructions for performing the processes described herein. In one embodiment, the at least one processor is a computing device capable of receiving, executing, and transmitting a plurality of programmatic instructions stored on a volatile or non-volatile computer readable medium. In addition, the software comprised of a plurality of programmatic instructions for performing the processes described herein may be implemented by a computer processor capable of processing programmatic instructions and a memory capable of storing programmatic instructions.

Definitions

As used throughout this specification, the term 'IONM' systems refers to Intraoperative Neuromonitoring Systems used for the monitoring of the central and peripheral nervous systems while patients are undergoing surgical procedures.

As used throughout this specification, the term 'EEG' refers to Electroencephalography which is an electrophysiological monitoring method to record electrical activity of the brain.

As used throughout this specification, the term 'electrosurgical unit' or ESU refers to devices used for electrosurgery, including monopolar, bipolar, and monopolar/bipolar units, such as electrocautery devices. These systems typically include an electrosurgical generator (i.e. power supply, waveform generator) and a handpiece including one or several electrodes. By way of example, in monopolar electrosurgery, tissue may be cut and coagulated by completion of an electrical circuit that includes a high-frequency oscillator and amplifiers within the ESU, the patient, the connecting cables and the electrodes. In most applications, electric current from the ESU is conducted through the surgical site with an active cable and electrode. The electrosurgical current exits the patient through a dispersive electrode (usually placed on the patient at a site remote from the surgical site) and its associated cable connected to the neutral side of the generator. In bipolar electrosurgery, two electrodes (generally, the two tips of a pair of forceps or scissors) serve as the equivalent of the active and return electrodes in the monopolar mode.

As used throughout this specification, the term 'electrocautery' refers to a process in which a direct or alternating current is passed through a resistant metal wire electrode, generating heat. The heated electrode is then applied to living tissue to achieve hemostasis or varying degrees of tissue destruction.

As used throughout this specification, the term 'input saturation' refers to an input level that has exceeded a system threshold, thereby causing the system to be non-responsive, unstable, or unable to properly process the input.

As used throughout this specification, the term 'gain' refers to a ratio of two quantities, namely an output of a circuit relative to an input of the circuit, thereby representing an amplification or decrease of an input signal.

As used throughout this specification, the term 'electrical transients' refers to momentary bursts of energy induced upon an electrical circuit. These bursts can be caused by electrical static discharge or another external source. They are characterized by extremely high voltages that drive high amounts of current into an electrical circuit for a few millionths of a second up to a few thousandths of a second.

Noise Detection in IONM Systems

The noise detector described in the present specification detects high frequency noise in patient signals obtained from patient electrodes of the IONM system. In various embodiments, the noise detector uses a capacitively coupled signal between isolated ground and non-isolated ground.

It should be noted herein that, as used in the present specification, capacitive coupling refers to joining two circuits such that the AC current from a first circuit is able to pass through to a second circuit while the DC current is blocked. In an embodiment, the first circuit is the isolated circuit that is connected to the patient. In an embodiment, the source of the signal to the first circuit is the electrosurgical current on the patient. In an embodiment, the second circuit is the non-isolated circuit that is connected to ground (earth). An advantage to coupling isolated ground and non-isolated ground in this manner is that patient isolation can be maintained but AC currents can still be gathered from the patient through capacitive coupling. The non-isolated circuitry positioned within the equipment is substantially stable during electrosurgical activity while the isolated ground follows the patient with respect to earth ground. In addition, because the communication link between isolated and non-isolated circuits can become corrupted if the electrosurgical noise is strong enough, by referencing to earth ground and implementing the detection on the non-isolated circuit, the embodiments of the present specification are still capable of noise detection and communication to a computing system since the non-isolated communication links remain stable.

FIG. 1 is a block and circuit flow diagram of a system 100 for determining high frequency noise causing interference in patient signals when a surgical procedure is being performed on a patient 101 being monitored by an IONM system, in accordance with some embodiments of the present specification. In various embodiments, high frequency noise refers to signals having frequencies greater than 100 kHz. In an embodiment, system 100 comprises an ESU (Electrosurgical Unit) 102, a plurality of electrodes 103 contacting the patient 101, first circuit 105 comprising an isolated ground plane, over which a portion of second circuit 110 comprising non-isolated circuitry is positioned to form capacitance 106, wherein the portion preferably comprises a copper pad. In embodiments, the second circuit 110 comprises high frequency noise interference detection circuitry. In embodiments, ESU 102 is in electrical contact with the first circuit 105 (isolated ground) through patient 101 and the plurality of electrodes 103. The capacitance between the isolated ground plane first circuit 105 and the copper pad of the second circuit 110 enables the AC voltage on the first isolated ground circuit 105 to inject AC current into the non-isolated second circuit 110 when the ESU 102 is active. Thus, as a result of capacitive coupling, ESU current from the first circuit 105 (that is, the isolated circuit) passes through to the second circuit 110 through capacitance 106.

In accordance with aspects of the present specification, there are two signal processing paths in second circuit 110. In the first signal processing path 111a, the patient signals are processed by passing through a primarily hardware-based detector solution 120 whereby the resultant signals are input into a first analog to digital (ADC) converter at pin 115 on a non-isolated processor or microcontroller 116. In some embodiments, the hardware-based detector solution 120 includes a delay circuit configured to detect high frequency noise (frequencies greater than 100 kHz) that occur with a high rate of occurrence (30 kHz and above). In the second signal processing path 111b, the patient signals are passed through a hardware high-pass filter 132 and the resultant signals are input into a second analog to digital (ADC) converter at pin 117 on the non-isolated microcontroller 116. The function of the second signal processing path is described as a primarily firmware-based detector solution 130 as most of the computation is done in the processor 116 of the IONM system. In some embodiments, the firmware-based detector solution 130 is configured to detect high frequency noise (frequencies greater than 100 kHz) that have any rate of occurrence. Therefore, the firmware-based detector solution 130 is not dependent on a high rate of occurrence to detect high frequency noise. In embodiments, system 100 allows for the signals to pass through either the first signal processing path 111a or the second signal processing path 111b. In embodiments, the IONM system may include both ESU detector solutions 120 and 130 or just one of the solutions. In embodiments, the first signal processing path 111a has an advantage of requiring less computation in the firmware which allows for lower latency for detection of noise and lower clock speeds in the processor compared to the second processing path 111b, while the second processing path 111b comprises fewer components for implementation compared to the first processing path 111a.

In some embodiments, the hardware circuit 120 comprises, in relation to the first signal processing path, an N pole high pass filter 122 to remove unwanted low frequency signals (signals having frequencies less than 100 kHz) and output a filtered signal, a gain circuit 124 to apply optional gain to the filtered signal and output a gained signal, a rectifier circuit 126 that provides rectification of the gained signal and outputs a DC (Direct Current) voltage signal, a delay circuit 128 to condition the DC voltage signal by attenuating contribution from periodic signals with high frequencies occurring at low rates, and a low pass filter 129 to remove high frequency noise from the DC voltage. Thus, in accordance with an aspect of the present specification, the hardware circuit 120 acquires AC current from ESU activity on the isolated ground circuitry 105 and conditions or processes the signal to produce a DC voltage for input to the first analog to digital (ADC) converter at pin 115. Unwanted frequencies and waveforms are filtered out and a DC threshold is used to determine ESU activity. In some embodiments, the system 100 provides for an increased degree of signal uniformity as the DC threshold does not suffer from spikes since the frequencies are filtered.

It should be noted that through the second signal processing path 111b the microcontroller 116 samples the signal transmitted by the AC currents from the isolated ground circuitry 105 at a higher sampling frequency or clock speed to determine frequencies and/or variance of the signal. In contrast, the first signal processing path 111a provides a DC voltage with a threshold to determine ESU activity. Periodic signals with high frequencies but low rate of occurrence (that is, electrical simulator artifact or similar) are attenuated in a manner so that they do not contribute to DC voltage. Also, sampling (at the microcontroller 116) can be done at a low sampling frequency or clock speed and a DC threshold can be used to determine ESU activity.

Hardware-Based Detector

As described above, the system of the present specification, in an embodiment, involves a primarily hardware-based solution for determining ESU activity on a patient signal. In embodiments, the hardware circuit is configured to enable sampling of signals from patient-isolated circuitry to provide a DC voltage threshold that can be used to determine ESU activity on the patient signal. Using the hardware circuit, unwanted low frequency signals are filtered out, the contribution from periodic signals with high frequencies but low rate of occurrences (that is, electrical stimulation artifact) is attenuated, and high frequency noise on DC voltage is filtered out, providing a simple DC threshold detection strategy. In embodiments, the hardware circuit processes the AC signal (from the patient isolated circuitry) across an isolation barrier with a delay circuit configured so that the circuit is charged by an ESU sourced signal and not by an electrical stimulation sourced signal.

This approach has several distinct benefits from similar prior art solutions. Firstly, the hardware based solution of the present specification includes multiple high-pass filter poles to further attenuate low frequency interference. Secondly, the hardware based solution allows for amplification of the signal, thereby increasing the dynamic range of the DC output voltage. Thirdly, the hardware based solution intrinsically attenuates signals with high frequencies but low rate of occurrences, such as electrical stimulator artifacts, thereby decreasing those signals' contribution to the DC voltage. The hardware based solution also allows for a low-pass filter on the DC output, thereby reducing error from sampling high frequency noise peaks.

Figure 2A:
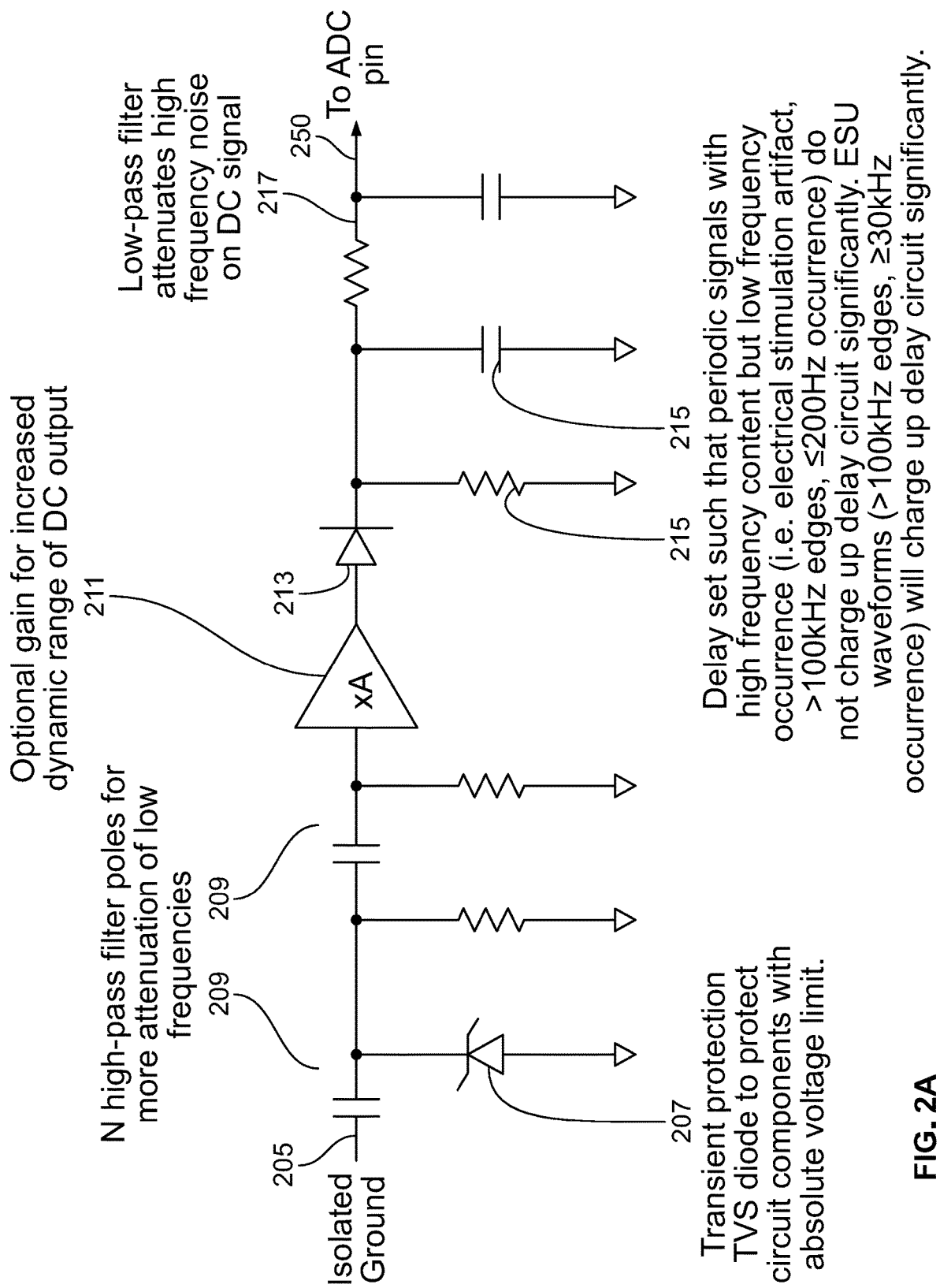
FIG. 2A illustrates hardware circuit elements of the primarily hardware-based solution shown in FIG. 1, in accordance with some embodiments of the present specification.

FIG. 2A illustrates hardware circuit elements of the first signal processing path 111a of the system 100 shown in FIG. 1, in accordance with some embodiments of the present specification. Referring now to FIGS. 1 and 2A, patient signals enter the path 111a at an input 205 and exit the path 111a at an output 250 to enter into the first analog to digital (ADC) converter at pin 115 on the non-isolated microcontroller 116.

In embodiments, a TVS (Transient Voltage Suppression) diode 207 provides transient protection of circuit components. Use of the TVS diode 207 in the systems of the present specification is different from a current limiting resistor as used in prior art. The TVS diode 207 has the advantage of providing absolute voltage limitation. Additional poles are added to an N pole high pass filter 209 to further attenuate low frequency signals and output the filtered signal. This provides a larger distinction between the low frequency signals and the high frequency ESU signals compared with prior art solutions.

A gain circuit 211 applies an optional gain to the filtered signal. This provides a larger dynamic range of the DC output voltage to minimize "false" positive detection. In some embodiments, the applied gain is of 1 or more. A rectifier circuit 213 provides rectification of the signal for DC voltage.

A delay circuit 215 attenuates contribution from periodic signals with high frequencies but low rate of occurrence. In some embodiments, timing of the delay circuit 215 is configured such that periodic signals with high frequencies but low rate of occurrence (for example, electrical stimulation artifacts with frequencies greater than 100 kHz and a rate of occurrence less than or equal to 200 Hz) do not charge up the delay circuit 215 significantly and therefore do not significantly raise the DC voltage. ESU signals with frequencies greater than 100 kHz and nominally greater than or equal to 30 kHz rate of occurrence will significantly charge up the delay circuit and therefore significantly raise the DC voltage. This reduces the number of software algorithms needed to filter out this type of interference to prevent "false" positive detection. Finally, a low pass filter 217 attenuates high frequency noise to prevent erroneous readings of DC voltage. This reduces the need to average samples and lowers the chance of "false" positive detection.

Figure 2B:
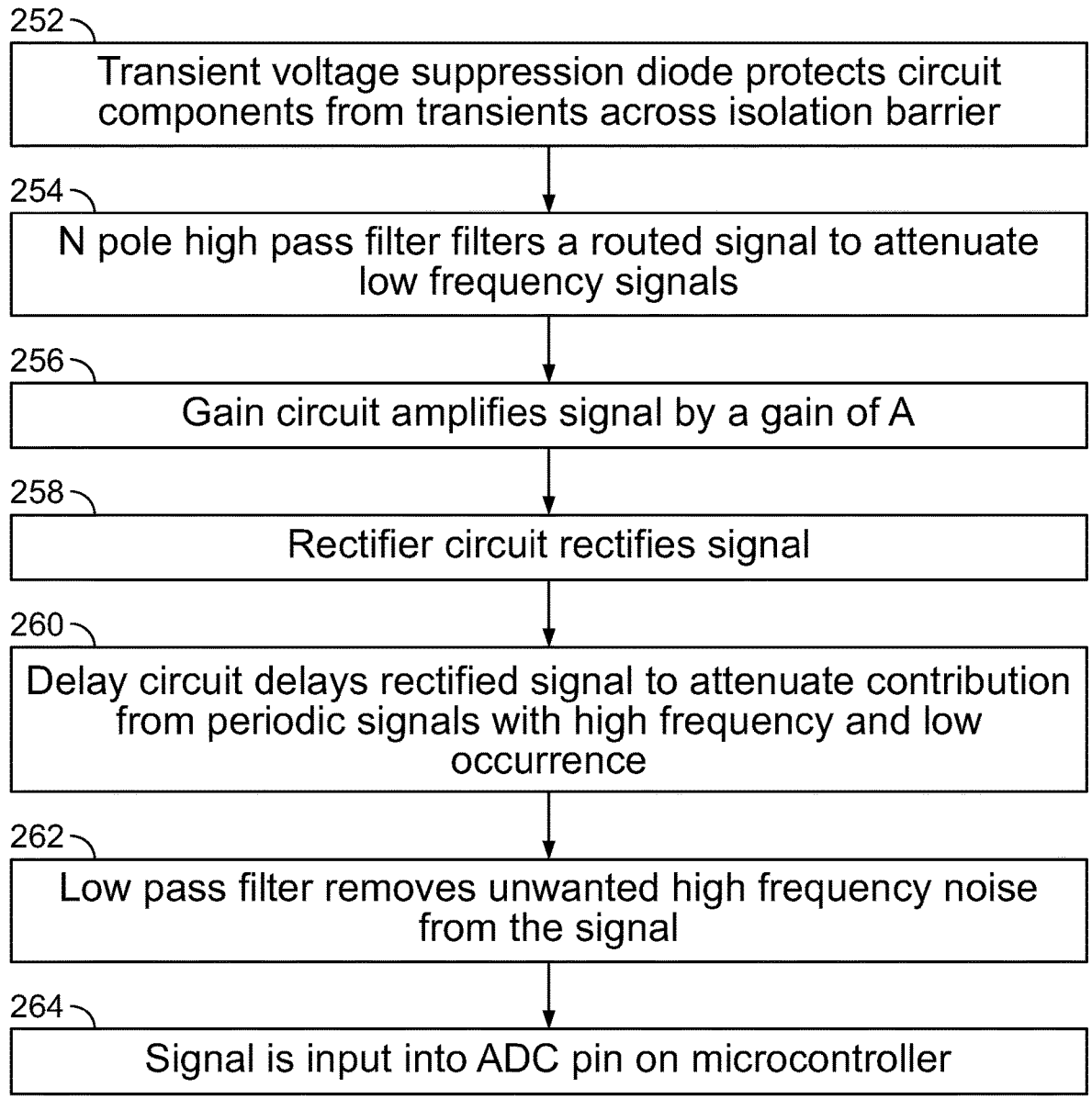
FIG. 2B is a flowchart illustrating the steps in a method of detecting a high frequency noise causing interference on patient signals being monitored by an IONM system using the hardware circuit elements of FIG. 2A, in accordance with some embodiments of the present specification.

FIG. 2B is a flowchart illustrating the steps in a method of detecting a high frequency noise causing interference on patient signals being monitored by an IONM system using the hardware circuit elements of FIG. 2A, in accordance with embodiments of the present specification. Referring now to FIGS. 2A and 2B, at step 252, during operation, the TVS (Transient Voltage Suppressor) diode 207, referenced to non-isolated or Earth ground, protects the circuit components from electrical transients across the isolation barrier. The signal routes through the N pole high pass filter 209 to attenuate unwanted low frequencies at step 254. This signal is amplified by a gain of 'A' by the gain circuit 211 at step 256 and then rectified by the rectifier circuit 213 at step 258.

The delay circuit 215 delays the rectified signal appropriately at step 260 to attenuate contribution from periodic signals with high frequencies but low rate of occurrence (that is, electrical stimulation artifact >100 kHz frequency content and ≤200 Hz occurrence rate) while allowing ESU signals with >100 kHz frequencies and ≥30 kHz occurrence rate to contribute significantly to the DC voltage. It should be appreciated that the delay circuit attenuates contribution from periodic signals with frequencies having a first range of wavelengths that occur at a first rate of occurrence while allowing ESU signals with frequencies having a second range of wavelengths that occur at a second rate of occurrence (where the second rate of occurrence is greater than the first rate of occurrence) to contribute significantly to the DC voltage.

The DC signal is then sent through the low pass filter 217 at step 262 to remove unwanted high frequency noise before connecting to, or being input into, an analog to digital (ADC) converter at a pin on a non-isolated microcontroller at step 264. The non-isolated microcontroller can sample at a low frequency or clock speed and use a predefined DC threshold value to determine ESU activity on a patient. Thus, if the DC value exceeds the threshold value for a predefined period of time, an alarm status in the IONM system is set to a "true" state indicative of a detection of noise associated with the ESU. On the other hand, if the DC value does not exceed the threshold value then the alarm status in the IONM system is set to a "false" state indicative of no detection of noise associated with the ESU.

Firmware-Based Detector

As described above, the system of the present specification, in an embodiment, involves a primarily firmware-based solution for determining ESU activity on a patient. In embodiments, a hardware circuit is configured to enable sampling of signals from patient-isolated circuitry to provide AC waveform data to be processed for detection of ESU activity. In an embodiment, this signal is digitized or sampled at 200 Hz on the non-isolated side. In an embodiment, an IONM system firmware runs the data through an exponentially weighted variance calculation. The variance calculation results are compared with a threshold to determine an alarm state in the IONM system. Upon acquiring a new signal sample being received by the IONM system input, the sample is added to a running variance calculation, and the updated variance is compared to a configurable noise threshold level. In an embodiment, the variance computation is performed at a firmware level in order to minimize the latency from a noise interference event and detection at the host level. The latency involved with host side processing may be undesirable in some instances as the patient data with noise interference could already have been processed before the host PC detected the interference event. The firmware is programmed to update the calculation as soon as a new signal sample is available and send status updates immediately on determining any signal state changes. The variance threshold and "forget factor" are configurable from the host software. In an embodiment, the "forget factor" represents a weighting factor that determines how much weight is given to older samples. Stated differently, the "forget factor" is used to determine how quickly the running variance calculation "forgets" old data.

Figure 3A:
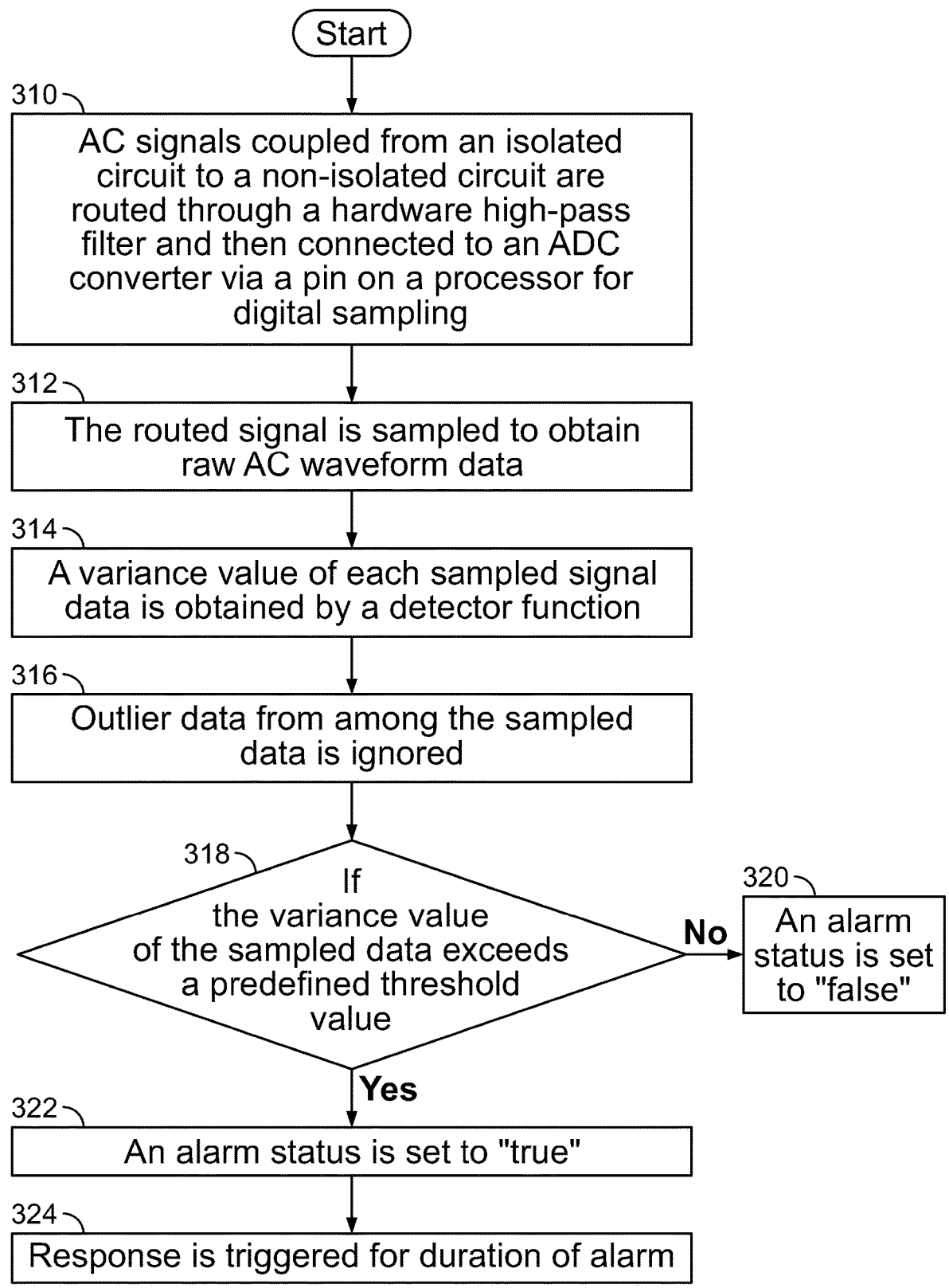
FIG. 3A is a flowchart illustrating the steps of a method for detecting interference in input patient signals being monitored by an IONM system, using the primarily firmware-based detector solution shown in FIG. 1, in accordance with an embodiment of the present specification.

FIG. 3A is a flowchart illustrating the steps in a method of detecting a high frequency noise causing interference on patient signals being monitored by an IONM system using the second signal processing path 111b of the system 100 shown in FIG. 1, in accordance with some embodiments of the present specification. This embodiment describes the primarily firmware-based detector solution 130 as shown in FIG. 1. Referring to FIG. 1, after the input signal passes through the hardware high-pass filter 132, the signal is routed to the analog to digital (ADC) converter at pin 117 of the microcontroller 116. The corresponding sampled raw data is fed into a detector function, which is processed by the firmware of the IONM system.

Referring now to FIGS. 1 and 3A, at step 310, AC signals coupled from the isolated circuit 105 to the non-isolated second circuit 110 are routed through the hardware high-pass filter 132 and then connected to the analog to digital (ADC) converter at pin 117 on the microcontroller 116 of the IONM system. At step 312 the routed signal is sampled by the processor 116 to obtain raw AC waveform data.

At step 314, a variance value of each sampled signal data is obtained by a detector function processed by the firmware of the IONM system. In an embodiment, a variance value of each sampled input signal is determined by the detector function and, if a variance value exceeds a predefined threshold value, a noise interference condition is indicated.

At step 316, outlier data from among the sampled data is ignored. In an embodiment, a data point is considered an outlier if the resulting increase in the variance is considerably larger than the previous variance value over a given time window. Hence, a single point over a small period of time that significantly increases the variance is omitted from the calculation used for determining an alarm state but, if a subsequent point in the same time window significantly increases the variance, it is deemed valid. Removing outlier data significantly reduces "false" alarm rate during implementation of the detector function. The time window and the outlier threshold are both configurable from the host software. In an embodiment, the host software is the software that is running on the computing system. In embodiments, the configuration parameters are established and set up by the user in the host software and communicated to the firmware for use in the calculations.

At step 318 it is determined if the variance value of the sampled data exceeds a predefined threshold value. Upon acquiring a new signal sample, the signal sample may be added to a running exponentially weighted variance calculation, and an updated variance value may be compared to a predefined threshold value. The detector function sends a status update to the host at nominally 1 Hz. The function sends a flag: "true" for threshold exceeded (alarm state) and "false" for threshold not exceeded (non-alarm state). Additionally, the function is programmed to send a status update immediately (i.e. not wait for the next 1 Hz update) if the state changes from "false" to "true".

The detector function also provides an "alarm hold-off time" which determines how long after the last alarm condition detected should the status flag be cleared back to the non-alarm state. If the detection threshold exceeds a predefined value, the function is programmed to continue to report a "true" status until the threshold value is not exceeded (i.e. the signal variance remains below the threshold value) for a minimum of the alarm hold-off time. If the threshold is exceeded again during the hold off time, the time is restarted. The hold-off time is useful for cases where activities causing interference are not continuous in the absolute sense but instead come in bursts. In an embodiment, the hold-off time is defaulted to 3000 milliseconds.

At step 320, an alarm status is set to "false" if the variance value does not exceed the predefined threshold value. At step 322 an alarm status is set to "true" if the variance value exceeds the predefined threshold value indicating a noise interference condition. In an embodiment, if an alarm is detected, one optional step 324 comprises triggering a response for the duration of the alarm. In embodiments, the response comprises one or more of notifying a user of the detected alarm and applying a limitation to the processing of incoming patient data. For example, the system may exclude incoming patient data from a running average. Similarly, if acquired patient data is being converted to audio, the response may comprise disabling audio output to prevent undesirable high frequency tones to be heard. When the detector indicates that the alarm condition no longer exists, acquisition and processing resume as normal.

Figure 3B:
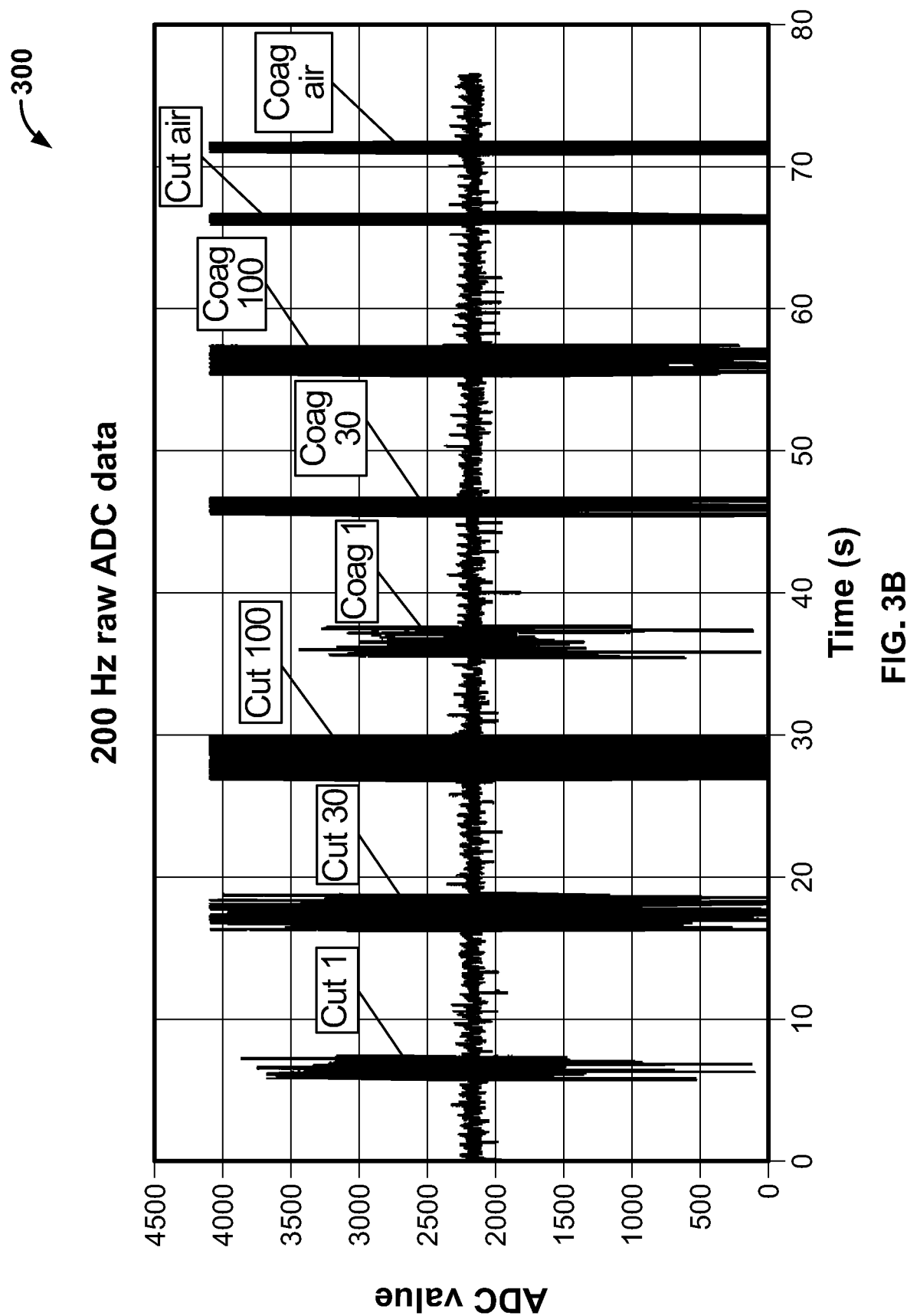
FIG. 3B is a plot showing raw ADC signal data sampled at 200 Hz, in accordance with an embodiment of the present specification.
Figure 3C:
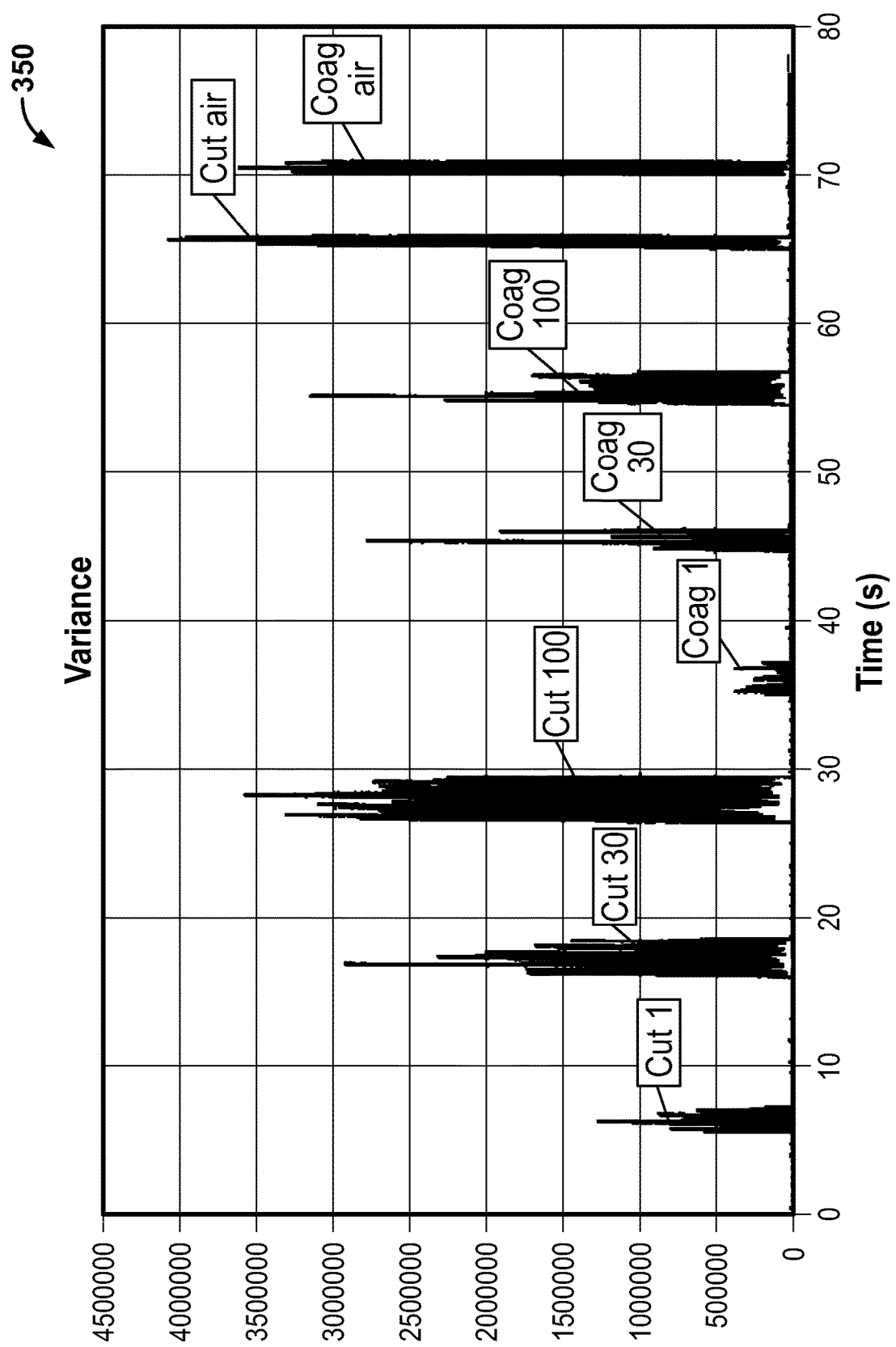
FIG. 3C is a plot showing the signal to noise ratio of the raw ADC signal data sampled at 200 Hz shown in FIG. 3B.

FIG. 3B illustrates a plot showing raw ADC (Analog to Digital) signal data sampled at 200 Hz, in accordance with an embodiment of the present specification. The plot 300 has been acquired by using the IONM system, placing a plurality of electrodes in a container of saline, and activating the ESU at predefined power levels and modes as indicated in the plot 300. In an embodiment, an exponentially weighted variance, as described by Tony Finch in "Incremental calculation of weighted mean and variance" (2009), is used to sample said signal data and obtain the plot 350 in FIG. 3C. In an embodiment, the exponentially weighted variance is initialized with a "forget factor" of 20 msec. The plot 350 in FIG. 3C shows the signal to noise ratio of the raw ADC signal data sampled at 200 Hz shown in FIG. 3B. This plot illustrates that the signal to noise ratio affords enough margin for detecting low power level settings on the ESU.

Figure 4A:
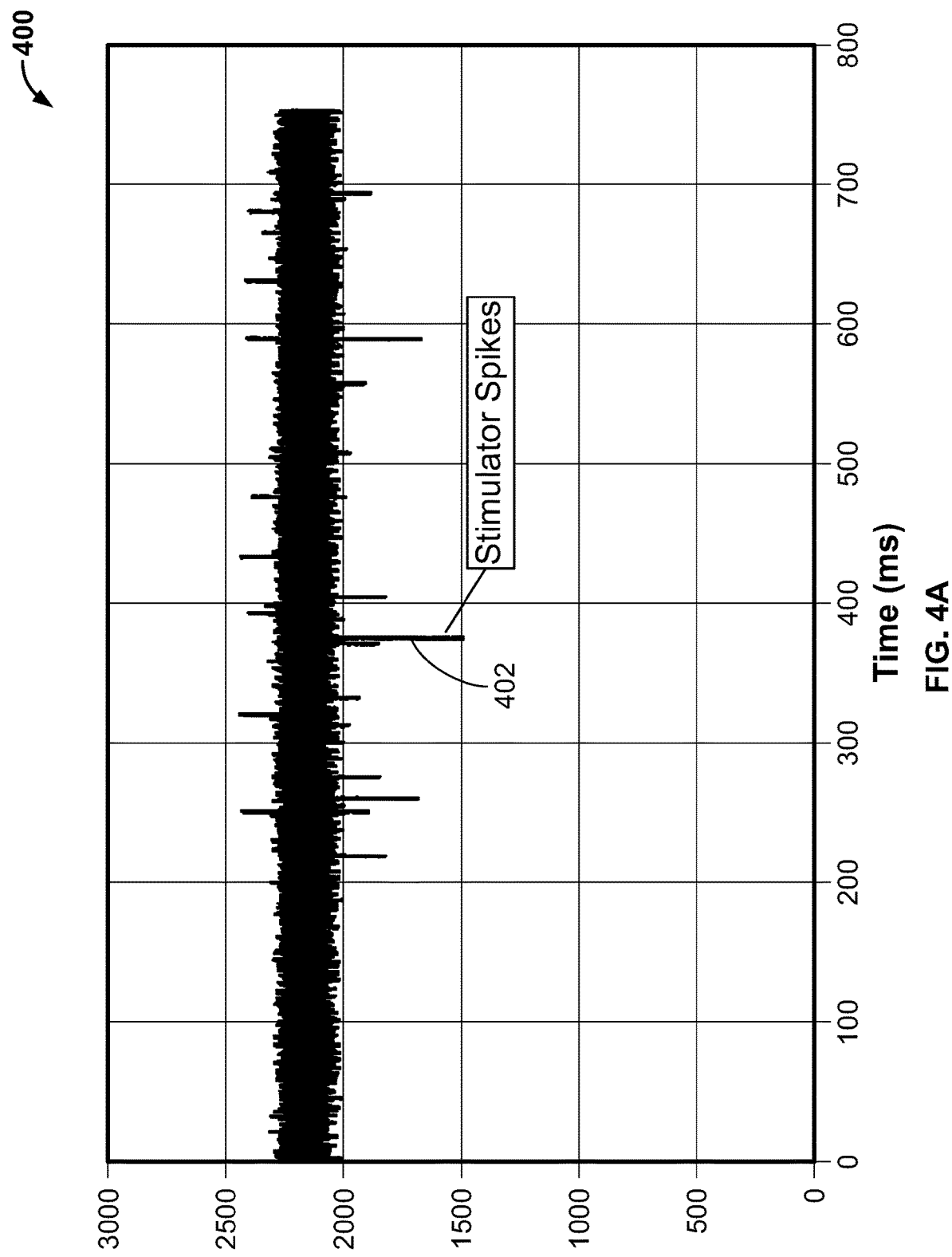
FIG. 4A is a plot showing raw data from a recording device of an IONM system used during testing, in accordance with an embodiment of the present specification.
Figure 4B:
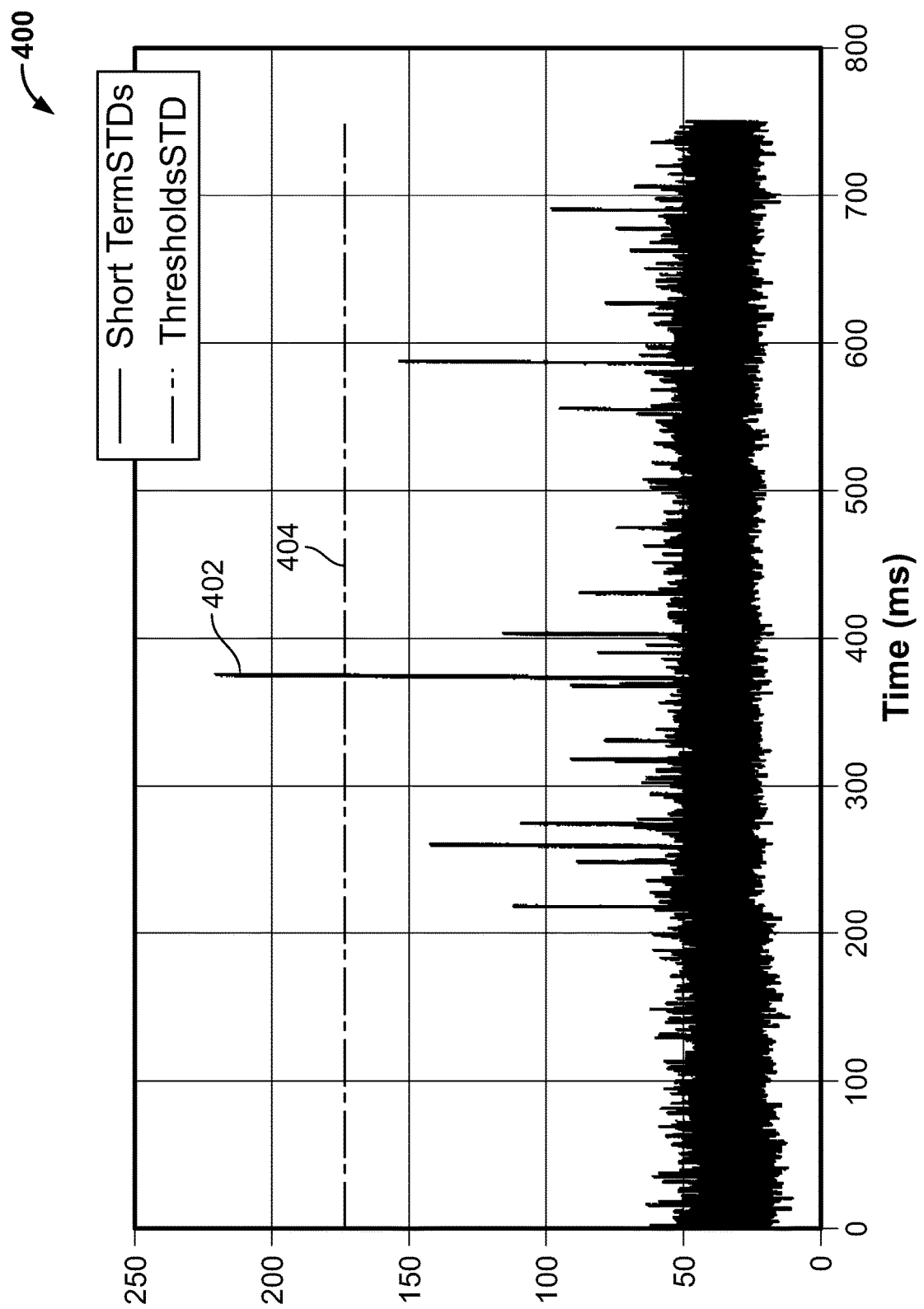
FIG. 4B is a plot showing a threshold being exceeded by the variance values of the data shown in FIG. 4A, without outlier detection.
Figure 4C:
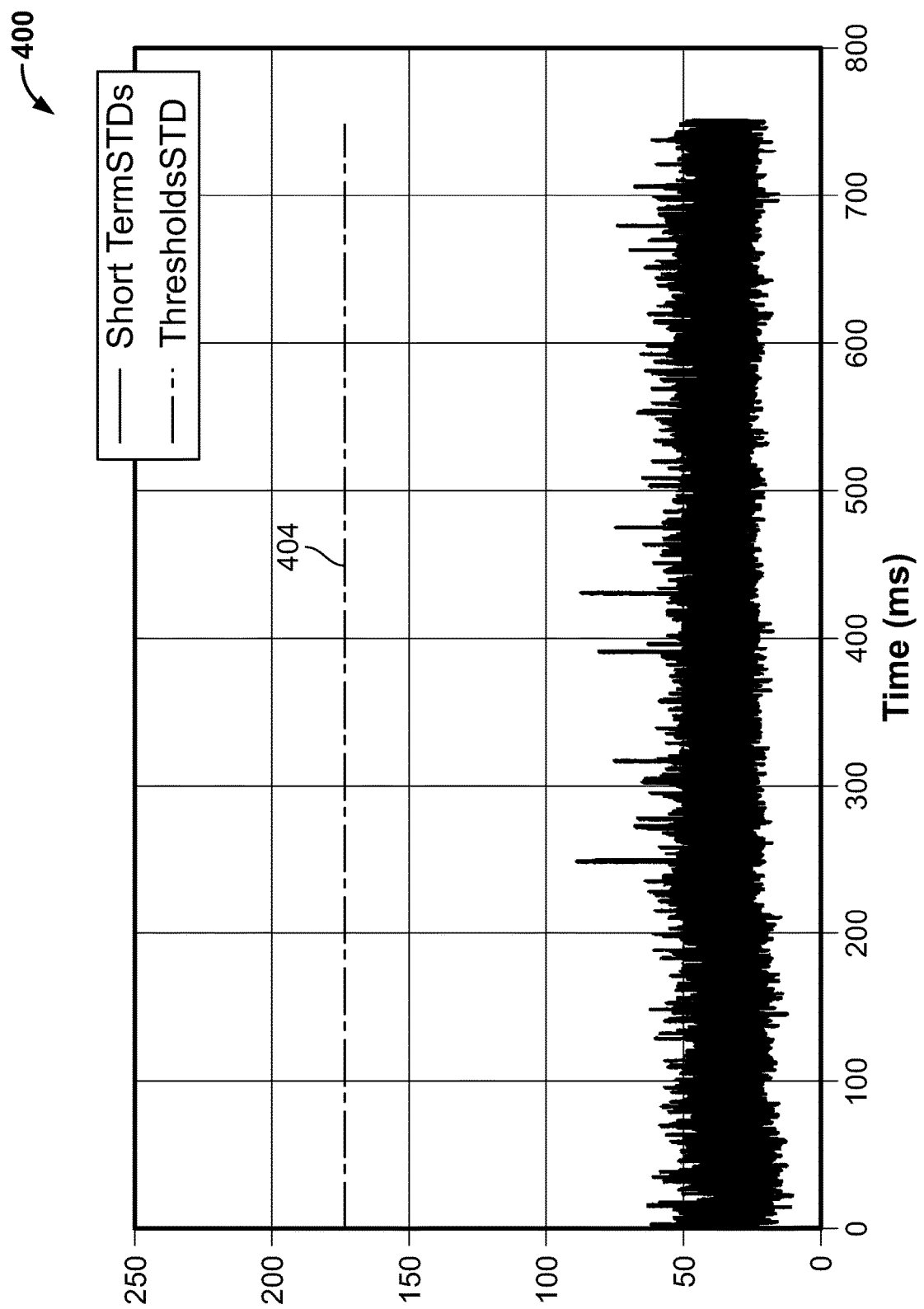
FIG. 4C is a plot illustrating the raw data of FIG. 4A not exceeding the threshold after outlier detection is applied to the data, in accordance with an embodiment of the present specification.

FIG. 4A illustrates a plot showing raw data from a recording device used during testing, in accordance with an embodiment of the present specification. This recording device is a component of an intraoperative neurophysiological monitoring system and involves the multi-modal recording of electrical potentials from the patient's body. Data from the recording device is shown in plot 400, which depicts spikes 402 in the data due to electrical stimulation. FIG. 4B illustrates a plot showing a threshold 404 being exceeded by the variance values of the data shown in FIG. 4A due to the spikes 402 from electrical stimulation. The threshold 404 is exceeded in this case as shown, and would cause an alarm state even though ESU activity is not present. FIG. 4C illustrates the raw data of FIG. 4A not exceeding the threshold after outlier detection is applied to the data. The data points considered outliers are rejected from the calculation, and the detector does not report an alarm state as the threshold 404 is not exceeded.

Input Saturation Detection and Resolution

Figure 5:
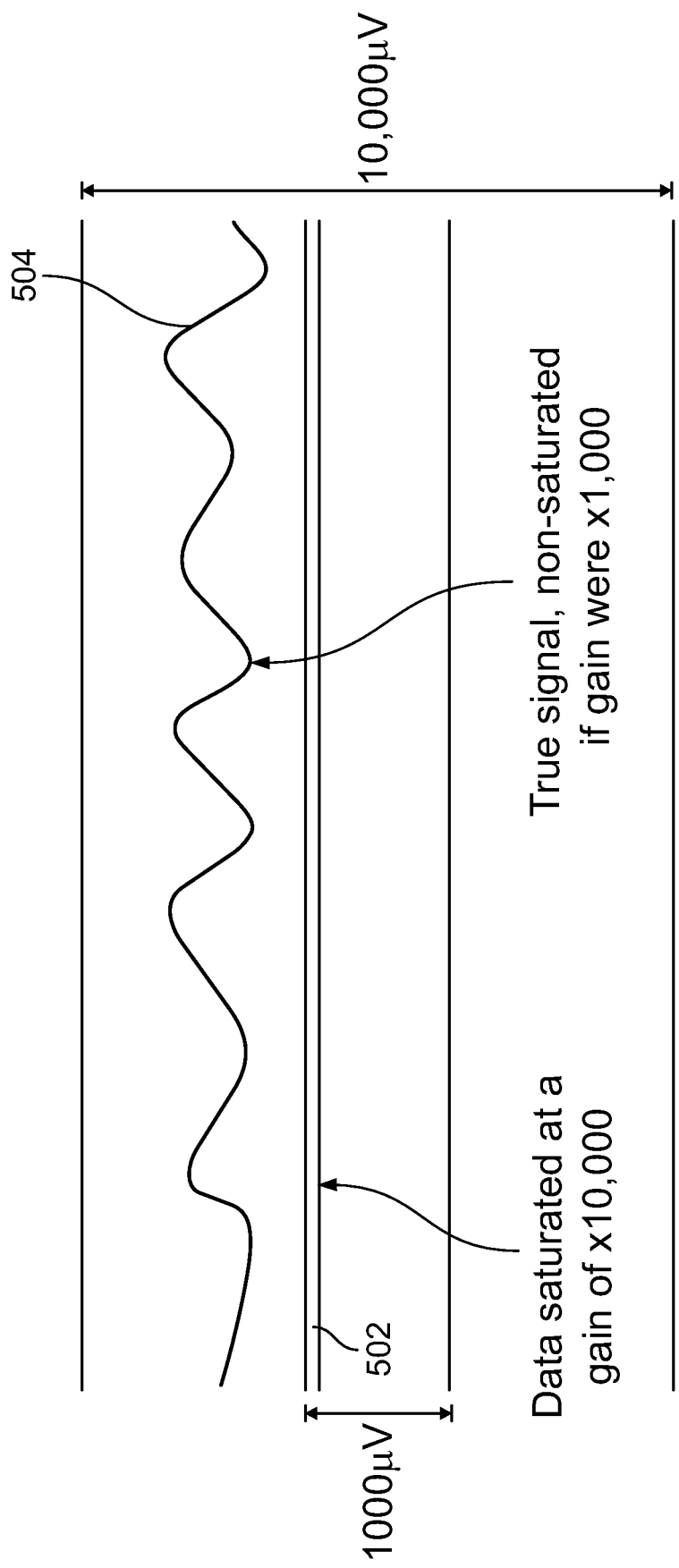
FIG. 5 is a diagram illustrating an input signal of an IONM system that is saturated with a hardware gain in the range of 10,000 that would not be saturated with a hardware gain in the range of 1,000.

Buildup of charge in patient electrodes can cause referential recording device inputs to become saturated if the hardware gain is very high (for example if the gain is 10,000) and the high-pass filter cutoffs of the IONM system are very low. This charge accumulation can occur during an electrocautery procedure or can be caused by some other interference when the patient is undergoing IONM. If an input is saturated this means that the digital signal is "flatlined" at or near the absolute value of the maximum value possible. The higher the hardware gain of the input, the smaller the range of input signal that can be represented before becoming saturated. FIG. 5 is a graph illustrating an input signal of an IONM system that is saturated with a hardware gain of 10,000. As an example, the full range of the input signal is 1,000 µN at this gain. The charge accumulation can cause a prolonged saturation state in the referential recording device inputs if the hardware gain on those inputs is around 10,000. This state can persist even after the electrocautery or other interference has finished. Decreasing the hardware gain (for example, to a gain of approximately 1,000) eliminates the saturated state because this lower gain allows for a larger range of input signal. As an example, the full range of the input signal is 10,000 µV at a hardware gain of 1,000. This lower gain eliminates saturation but decreases the resolution of the input. When the inputs are no longer saturated, the lower hardware gain is no longer needed and so increasing the hardware gain increases the resolution once again. As shown in FIG. 5, plot 502 depicts data saturated at a hardware gain of 10,000 or more, whereas plot 504 depicts a "true" signal that would be available if the hardware gain is decreased to 1,000. Hence, if the hardware gain is decreased, then the "floating" signal depicted by plot 504 may be captured and processed. EEG data acquisition typically uses a very low high-pass filter cutoff and high hardware gain. The high-pass filter cutoff is typically chosen to be as low as possible to keep relevant frequencies while still blocking DC. The high hardware gain setting allows the data to be acquired at the highest resolution possible for signals with a typical magnitude of tens of microvolts peak-to-peak. Increasing the high-pass filter cutoff would adversely impact the low frequency bands in the data while decreasing the hardware gain would decrease the resolution. A decreased resolution makes the signal look blockier but preserves its general characteristics, especially if the hardware gain decrease is not too large.

Figure 6:
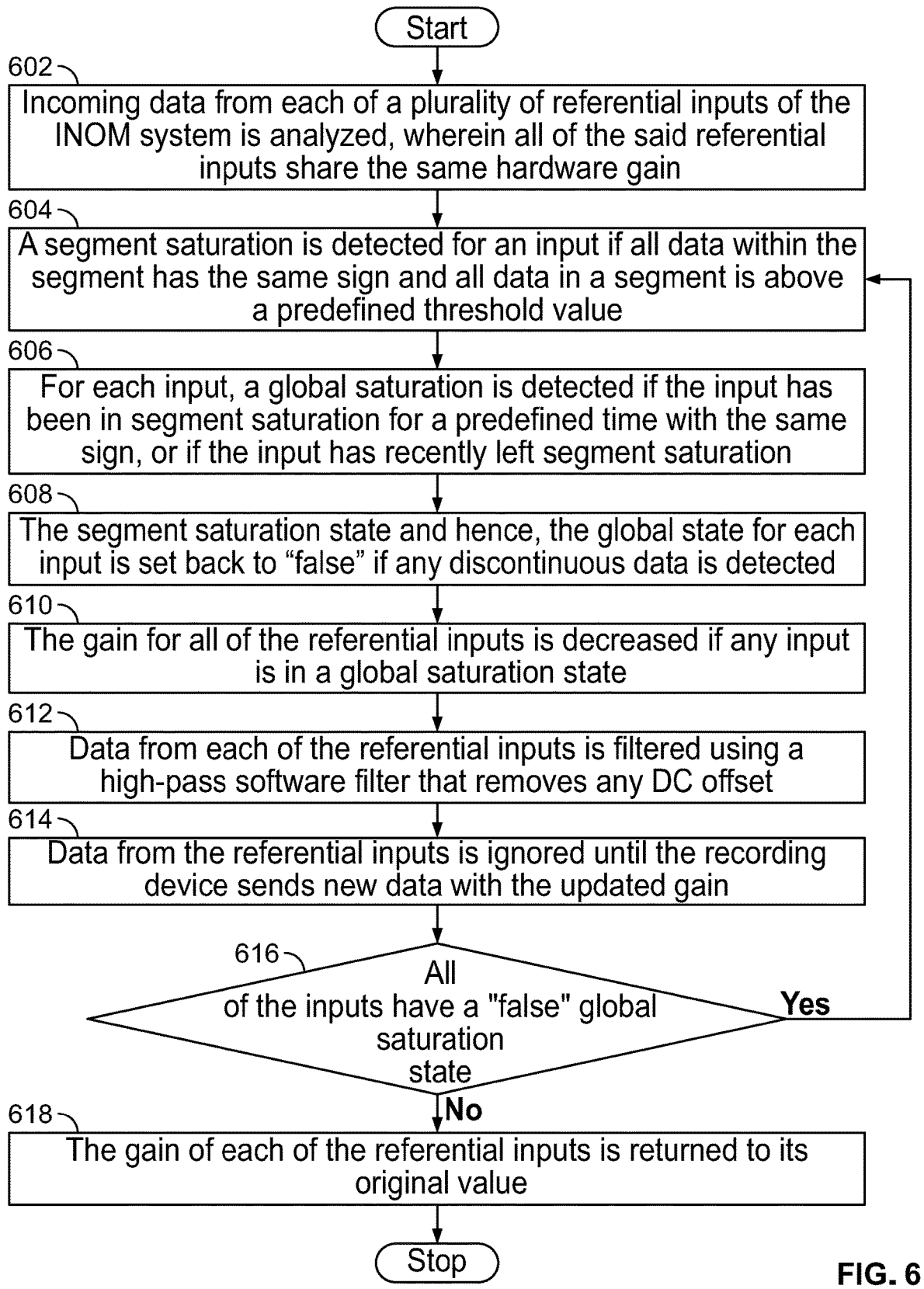
FIG. 6 is a flowchart illustrating the steps of a saturation detection method in an IONM system during an electrocautery procedure, in accordance with an embodiment of the present specification.

Therefore, the present specification provides a method for decreasing the hardware gain when saturation is detected and then increasing it at an appropriate time. One option is to limit the hardware gain changes during or immediately after ESU activity. This minimizes the data disruption if ESU is the only likely cause for saturation. If there are other causes for saturation, another option is to maintain the saturation detection and gain adjustment during all data acquisition. FIG. 6 is a flowchart illustrating the steps of a saturation detection method in an IONM system during an electrocautery procedure, in accordance with an embodiment of the present specification. The method of saturation detection in an IONM system may be implemented via an algorithm. It is assumed that all of the referential inputs are on the same recording device and share the same hardware gain in a given IONM system. It is also assumed that the inputs share the same high-pass filter cutoff when used for EEG so the inputs can be re-montaged.

Referring to FIG. 6, at step 602 incoming data from each of a plurality of referential inputs of the IONM system is analyzed, wherein all of the said referential inputs share the same hardware gain. In an embodiment, for each of the inputs, both the sign and amplitude of the data for successive data segments is monitored.

In an embodiment, a code object named 'amp' of type Amplifier is run on the recording device for implementing a saturation recovery algorithm of the present specification. When amp is constructed, a list of InputSaturationDetector objects, amp._inputSaturationDetectors, is created that contains saturation detectors for each referential input that has a high-pass filter cutoff at the lowest level and hardware gain at the highest level. If ESU activity is used as an input to the said method, the ESU activity is continually monitored by the recording device hardware and a notification is sent to the amp object when ESU activity has begun by calling amp.OnESUDetectionStarted( ) and when ESU activity has finished by calling amp.OnESUDetectionFinished( ) When ESU activity has finished, a timer, amp._postESUTimer, is started. ESU activity information can be acquired by either the primarily hardware-based detector solution or the primarily firmware-based detector solution as described above. If the input saturation and recovery algorithm is run during all data acquisition, ESU activity is not used to determine when to run the algorithm.

At step 604, a segment saturation is confirmed for an input if all data within the segment has the same sign (positive or negative) and all data in a segment is above a predefined threshold value. At step 606, for each input, a global saturation state is detected if the input has been in segment saturation for a predefined time with the same sign (positive or negative), or if the input has recently left segment saturation. Holding the global saturation state for an input helps to prevent frequent global saturation state changes that may impact data collection. Hence, the presence, and extent, of saturation for each input signal, is determined by determining how long the system has exceeded the predefined threshold value. At step 608, the segment saturation state and hence, the global state for each input is set back to "false" if any discontinuous data is detected.

In an embodiment, all incoming data blocks are acquired and processed by the method: amp.ProcessData( ). Each data block contains data for all referential inputs. If the algorithm is only enabled for ESU activity, a data block is analyzed for saturation only if amp is in saturation recovery (i.e. amp._isInSaturationRecovery is "true"), ESU is detected as active (i.e. amp._isESUDetected is "true"), or ESU activity has recently finished (i.e. the timer, amp._postESUTimer, hasn't reached its limit of amp.ESULimit seconds). If these conditions have not been met then each detector is reset and non-saturation processing continues. Otherwise, saturation detection proceeds. If saturation detection is enabled during all data acquisition and not just for ESU activity, the detection algorithm proceeds without the ESU related conditions being met. If data gaps have been detected between data blocks, then each detector is reset so that the saturation detection process will maintain its accuracy. The detectors are then updated. For each detector, the input for that detector is used to fetch the relevant data from the data block and the detector is updated. The update process sets a public property on the detector, IsSaturated, that is used to make decisions for saturation recovery in the Amplifier method ProcessSaturationRecovery( ).

At step 610, if any input is in a global saturation state the hardware gain for all of the referential inputs is decreased. In an embodiment, within ProcessSaturationRecovery( ) if any of the detectors report saturation through their IsSaturated property, then a local flag, isSaturated, is set to "true". Otherwise it is "false". A flag that is associated with the amp object, amp._isSaturationDetected, stores the saturation state for amp from the prior data block. The two flags are then compared. If isNowSaturated is "true" and _isSaturationDetected is "false", then the inputs are now saturated and the hardware gain on all referential inputs is decreased to the next available level. Otherwise, if isNowSaturated is "false" and _isSaturationDetected is "true", then the hardware gain is increased to the original level. The flag _isSaturationDetected is then updated to reflect the current state.

At step 612, the incoming data from each of the referential inputs is filtered using a high-pass software filter that removes any DC offset. Data from the referential inputs is ignored until the recording device sends new data with the updated hardware gain, at step 614. In an embodiment, there is one detector object dedicated to each input's data stream. The recording device input and ratio of low hardware gain to high hardware gain, known as GTF in InputSaturationDetector, are passed to the detector when the detector's Initialize( ) is called. Any time there is a break in saturation analysis, or if the incoming data stream is not contiguous, then the Reset( ) method must be called. The detector is updated through the Update( ) method. In addition to IsSaturated, there is an internal field that reports actual saturation of the current data segment, _S, and an intermediary field, _A that is used to determine the final value of IsSaturated. There is also a field, _sn, that reports the current sign of the data, whether positive or negative.

Steps 602 to 614 are repeated until it is determined if all of the inputs have a "false" global saturation state at step 616, which is when at step 618, the hardware gain of each of the referential inputs is returned to its original value. In an embodiment, an Update( ) function is executed wherein, the input data from the recording device is passed in as 16 bit signed integers ranging from −32,768 to 32,767. It is assumed that no preprocessing, such as filtering, has been performed. Also passed in is a flag, isInSaturationRecovery, that is "true" if the recording device is currently in saturation recovery and "false" otherwise. If isInSaturationRecovery is "true", then the recording device hardware gain has been increased and the threshold determining saturation, T, must be adjusted down by a factor of GTF. This is because the signal is no longer saturated at the new hardware gain, but it must be determined if it would be saturated at the higher hardware gain. The actual saturation of the current segment, x, is then determined. If the sign of all of the data points in x are the same and their absolute value is less than the threshold T, then they are saturated and _S is set to "true". The saturation threshold T is defined as 0.95×(32,767−517). The value of 517 was determined from experiments on positively saturated input data that showed the data was always under 32,767 when saturated. The value of 0.95 is a potentially adjustable sensitivity setting. If S is "true" for this segment but was "false" for the previous segment, then a transition has occurred to a "true" saturated state and a timer, _swlTimer, is restarted. If the current value of _swlTimer is greater than or equal to SWL, then the active saturation state, _A, is set to "true" and the timer is cleared. Otherwise it is set to "false". Whereas _S defines an individual segment's saturation state, _A defines the running saturation state. The wait period is needed to ignore a frequently changing saturation state, for example from ESU noise or other interference, and focus on steady-state saturation. If _A is "true" then IsSaturated is "true" as well. If _A is "false" for this segment but was "true" in the previous segment, then a transition was made to a non-saturated state and the saturation hold timer, _shlTimer, is restarted. If the current value of _shlTimer is greater than or equal to a limit, SHL, then IsSaturated is "false" and the timer is cleared. The second timer holds the reported saturation state in the presence of occasional drops in saturation.

In an embodiment, the method of FIG. 6 is performed only when an electrocautery procedure is in progress. In another embodiment, the method of FIG. 6 is performed during all data acquisition.

Figure 7:
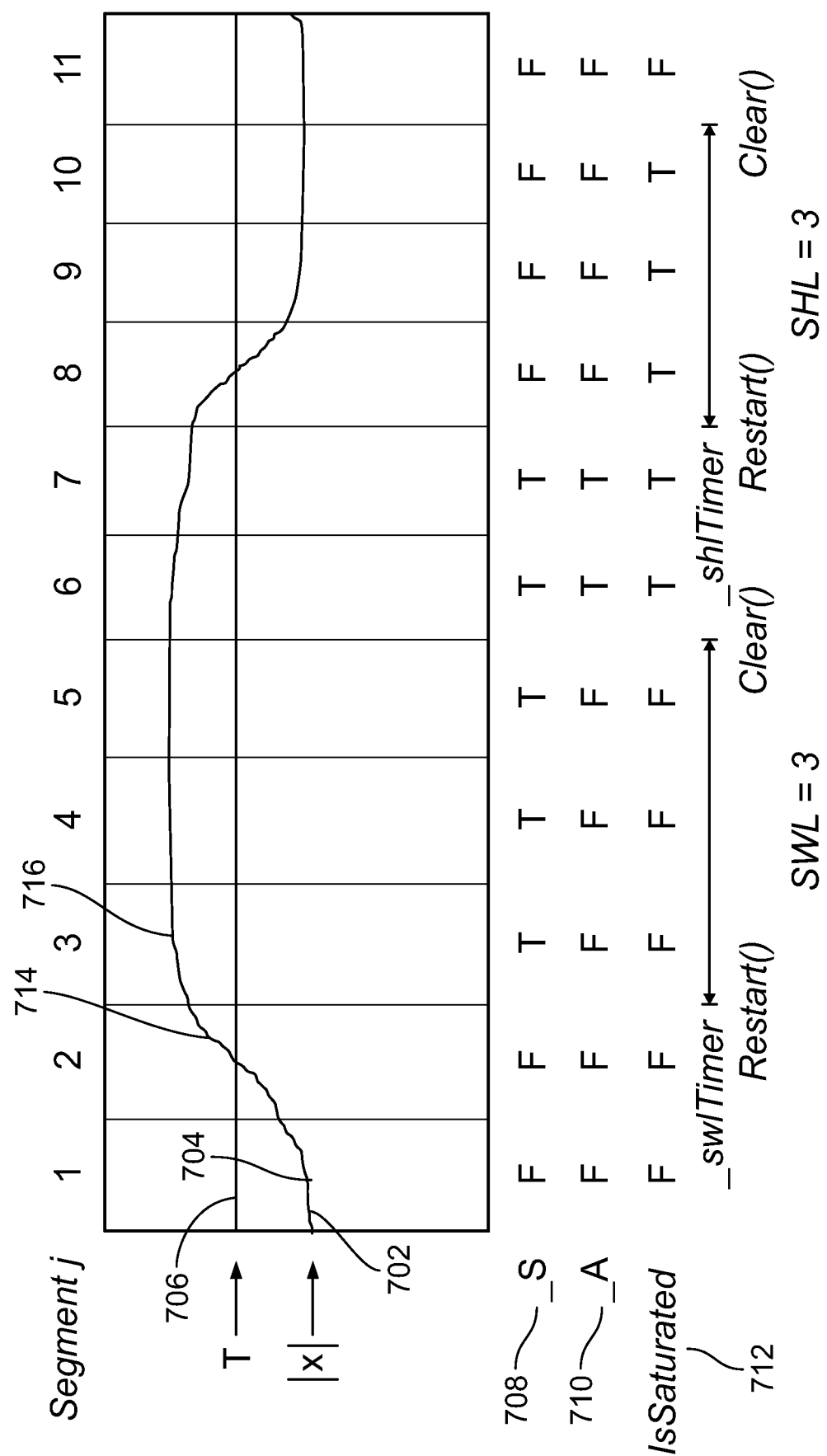
FIG. 7 is a pictorial representation of the results obtained upon processing an exemplary set of data by using the 'InputSaturationDetector' detector, in accordance with an embodiment of the present specification.

FIG. 7 is a pictorial representation of the results obtained upon processing an exemplary set of data by using the 'InputSaturationDetector' detector that contains saturation detectors for each referential input that has a high-pass filter cutoff at the lowest level and the hardware gain at the highest level. Plot |x| 702 depicts the data stream which is split into predefined segments, such as segments 1 through 11. In 'segment 1', |x| 704 is less than a threshold saturation value 706 depicted by 'T'. The segment is therefore not saturated, and hence, the values of all saturation fields _S 708, _A 710, and _IsSaturated 712 are set as "false" as shown.

In 'segment 2', |x| 714 is still not saturated as only part of |x| 714 is above the threshold saturation value T 706. In 'segment 3', however, |x| 716 becomes saturated as the value of |x| 716 is above T 706 and (to be assumed) its sign is the same in the entire segment. Hence, for |x| 716 the value of _S 708 is set to "true" and an _swlTimer is restarted. Even though _S 708 is "true" in segments 3, 4, and 5, _swlTimer has not reached SWL (denoted by 3 segments for illustration), so _A 710 is still "false". The timer reaches SWL in segment 6 and _A 710 and IsSaturated 712 are set to "true". The data stream |x| 702 loses saturation in segment 8, setting _S 708 and _A 710 to "false", and restarting _shlTimer. Once _shlTimer reaches SHL, IsSaturated 712 is finally set to "false".

The above examples are merely illustrative of the many applications of the system of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A system configured to detect noise causing interference with signals being monitored by an intraoperative neurophysiological monitoring (IONM) system in electrical communication with a patient, wherein said noise is characterized by frequencies greater than 100 kHz, the system comprising:
    a first circuit comprising an isolated ground plane electrically coupled, through the patient, to an electrosurgical unit in electrical communication with the patient; and
    a second circuit comprising a microcontroller, a first signal processing path and a second signal processing path, wherein at least a portion of the second circuit is positioned over the first circuit such that, during operation, a capacitance is formed between the first circuit and the second circuit, wherein the second signal processing path is configured to sample signals transmitted by the first circuit and direct the sample signals through an exponentially weighted variance function, and wherein the system is configured to use at least one of the first signal processing path or the second signal processing path to detect said noise.

2. The system of claim 1, wherein the portion of the second circuit comprises a copper pad.

3. The system of claim 1, wherein the microcontroller comprises a first analog to digital converter configured to receive signals from the first signal processing path.

4. The system of claim 1, wherein the second signal processing path comprises a high pass filter.

5. The system of claim 3, wherein the microcontroller comprises a second analog to digital converter configured to receive signals from the second signal processing path.

6. The system of claim 1, wherein the first signal processing path comprises an N pole high pass filter configured to remove unwanted low frequency signals below a predetermined threshold value and generate a filtered signal, and wherein the low frequency signals comprise signals having a frequency of 100 kHz or less.

7. The system of claim 1, wherein the first signal processing path comprises a rectifier circuit configured to rectify a filtered signal for direct current voltage.

8. The system of claim 1, wherein the first signal processing path comprises a delay circuit configured to not be charged by electrical signals having frequencies greater than 100 kHz.

9. The system of claim 8, wherein the delay circuit is configured to be charged by electrical signals having frequencies greater than 100 kHz.

10. The system of claim 1, wherein the first signal processing path comprises a low pass filter configured to remove said noise from direct current voltage.

11. The system of claim 1, wherein the first signal processing path is configured to provide a direct current voltage with a threshold to determine activity of the electrosurgical unit.

12. The system of claim 1, wherein the first circuit is an isolated circuit, wherein the second circuit is a non-isolated circuit, and wherein signals from the first circuit and signals from the second circuit are capacitively coupled.

13. The system of claim 12, further comprising a high pass filter configured to filter the coupled signals.

14. The system of claim 12, further comprising a rectifier circuit configured to rectify the coupled signals from the first circuit and the second circuit.

15. The system of claim 14, wherein the microcontroller is configured to sample the rectified signals to detect a direct current value of the rectified signals.

16. The system of claim 15, wherein the microcontroller is configured to compare the detected direct current value against a threshold value.

17. The system of claim 16, wherein the microcontroller is configured to indicate a detection of the noise based upon said comparison.

18. The system of claim 14, further comprising a delay circuit configured to delay the rectified signals.

* * * * *